(12) United States Patent
Chism, II

(10) Patent No.: US 7,391,507 B2
(45) Date of Patent: Jun. 24, 2008

(54) METHOD OF PHOTO-REFLECTANCE CHARACTERIZATION OF STRAIN AND ACTIVE DOPANT IN SEMICONDUCTOR STRUCTURES

(75) Inventor: William W. Chism, II, Austin, TX (US)

(73) Assignee: Xitronix Corporation, Austin, TX (US)

( * ) Notice: Subject to any disclaimer, the term of this patent is extended or adjusted under 35 U.S.C. 154(b) by 7 days.

(21) Appl. No.: 11/586,403

(22) Filed: Oct. 25, 2006

(65) Prior Publication Data

US 2007/0097370 A1    May 3, 2007

Related U.S. Application Data

(60) Provisional application No. 60/730,293, filed on Oct. 27, 2005, provisional application No. 60/831,363, filed on Jul. 17, 2006.

(51) Int. Cl.
*G01B 11/16* (2006.01)
*G01N 21/55* (2006.01)

(52) U.S. Cl. .......................... 356/32; 356/445

(58) Field of Classification Search ............... None
See application file for complete search history.

(56) References Cited

U.S. PATENT DOCUMENTS 3,982,207 A    9/1976    Dingle et al.

(Continued)

FOREIGN PATENT DOCUMENTS

WO    WO 2004/107026 A3    12/2004

OTHER PUBLICATIONS

"Dynamics of the plasma and thermal waves in surface-modified semiconductors (invited)," Alex Salnick and Jon Opsal, Rev. Sci. Inst. 74, 545 (2003).

(Continued)

*Primary Examiner*—Michael P. Stafira
(74) *Attorney, Agent, or Firm*—Vinson & Elkins LLP

(57) ABSTRACT

A new method of photo-reflectance characterization of strain and active dopant in semiconductor structures has been developed for characterization of physical properties of semiconductor structures. The underlying principle of the strain and active dopant characterization technique is to measure photo-reflectance signals occurring nearby to interband transitions in the semiconductor bandstructure and which are highly sensitive to strain and/or active dopant through the effect of the nanometer scale space charge fields induced at the semiconductor surface. To attain this, the present disclosure comprises an intensity modulated pump laser beam and a continuous wave probe laser beam, focused coincident on a semiconductor structure. The pump laser provides approximately 15 mW optical power in the NIR-VIS. The pump light is amplitude modulated by a signal generator operating in the range of 100 kHz-50 MHz. The probe beam is approximately 5 mW operating in the VIS-UV and is generally of wavelength nearby to strong optical absorptions in the semiconductor structure. The pump and probe are focused co-incident to a micrometer scale spot on the sample. Probe specular reflections are collected and the pump wavelength light is removed using a color filter. The remaining probe light is directed onto a photodiode and converted to an electrical signal. The probe AC signal then contains pump induced changes in the semiconductor material optical response. Phase sensitive measurement is performed on the photodiode output and the AC signal is divided by the DC reflectance signal. Thus photo-reflectance information is recorded as a function of probe wavelength, modulation frequency, pump intensity, and pump and probe polarizations.

19 Claims, 25 Drawing Sheets

U.S. PATENT DOCUMENTS

| | | | |
|---|---|---|---|
| 4,750,822 | A | 6/1988 | Rosencwaig et al. |
| 4,931,132 | A | 6/1990 | Aspnes et al. |
| 5,501,637 | A | 3/1996 | Duncan et al. |
| 5,536,936 | A | 7/1996 | Drevillon et al. |
| 5,757,671 | A | 5/1998 | Drevillon et al. |
| 6,195,166 | B1 | 2/2001 | Gray et al. |
| 6,211,961 | B1 | 4/2001 | Maris |
| 6,400,449 | B2 | 6/2002 | Maris et al. |
| 6,489,801 | B1 | 12/2002 | Borden et al. |
| 6,963,402 | B2 * | 11/2005 | Chism, II .................. 356/369 |
| 7,239,392 | B2 * | 7/2007 | Chism, II .................. 356/369 |

OTHER PUBLICATIONS

"Nondestructive profile measurements of annealed shallow implants," P. Borden, et al., J. Vac. Sci. Technol. B 18, 602 (2000).

"Dielectric response of strained and relaxed $Si_{1-x-y}Ge_xC_y$ alloys grown by molecular beam epitaxy on Si(001)," R. Lange et al., J. Appl. Phys. 80, 4578 (1996).

"Optical functions of ion-implanted, laser-annealed heavily doped silicon," G.E. Jellison et al., Phys. Rev. B 52, 14 607 (1995).

"Photo-reflectance characterization of GaAs as a function of temperature, carrier concentration, and near-surface electric field," A. Badakhshan et al., J. Vac. Sci. Technol. B 11, 169 (1993).

"Photo-reflectance study of photovoltage effects in GaAs diode structure," V.M. Airaksinen and H.K. Lipsanen, Appl. Phys. Lett. 60, 2110 (1992).

"Photo-reflectance studies of silicon films on sapphire," A. Giordana and R. Glosser, J. Appl. Phys. 69, 3303 (1991).

"Correlation between the photo-reflectance response at $E_1$ and carrier concentration in n- and p-GaAs," A. Badakhshan, R. Glosser, and S. Lambert, J. Appl. Phys. 69, 2525 (1991).

"Dynamics of photo-reflectance from undoped GaAs," H. Shen et al., Appl. Phys. Lett. 59, 321 (1991).

"Photo-reflectance study of surface Fermi level in GaAs and GaAlAs," H. Shen et al., Appl. Phys. Lett. 57, 2118 (1990).

"Generalized Franz-Keldysh theory of electromodulation," H. Shen and F.H. Pollak, Phys. Rev. B 42, 7097 (1990).

"Photo-reflectance study of Fermi level changes in photowashed GaAs," H. Shen, F.H. Pollak, and J.M. Woodall, J. Vac. Sci. Technol. B 8, 413 (1990).

"Electric field distributions in a molecular-beam epitaxy $Ga_{0.83}Al_{0.17}As/GaAs/GaAs$ structure using photo-reflectance," H. Shen, F.H. Pollak, J.M. Woodall, and R.N. Sacks, J. Vac. Sci. Technol. B 7, 804 (1989).

"Thermal and plasma wave depth profiling in silicon," Jon Opsal and Allan Rosencwaig, Appl. Phys. Lett. 47, 498 (1985).

"Photo-reflectance characterization of interband transitions in GaAs/AlGaAs multiple quantum wells and modulation-doped heterojunctions," O. J. Glembocki et al., Appl. Phys. Lett. 46, 970 (1985).

"Reflectance Modulation by the Surface Field in GaAs," R.E. Nahory and J.L. Shay, Phys. Rev. Lett. 21, 1569 (1968).

"Band-Structure Analysis from Electro-Reflectance Studies," B.O. Seraphin and N. Bottka, Phys. Rev. 145, 628 (1966).

"Optical Field Effect in Silicon," B.O. Seraphin, Phys. Rev. 140, A 1716 (1965).

"Field Effect of the Reflectance in Silicon," B.O. Seraphin and N. Bottka, Phys. Rev. Lett. 15, 104 (1965).

"Optical-Field Effect on Thresholds, Saddle-Point Edges, and Saddle-Point Excitons," J.C. Philips and B.O. Seraphin, Phys. Rev. Lett. 15, 107 (1965).

Aspnes, "Characterization of semiconductors and semiconductor structures by optical techniques/optical properties of materials and structures," SPIE, Oct. 1990.

Aspnes, "Observation and analysis of epitaxial growth with reflectance-difference spectroscopy," Materials Science and Engineering B30, 109-119, 1995.

Klar et al., "Photomodulated reflectance study of $In_xGa_{1-x}As/BaAs/AlAs$ microcavity vertical-cavity surface emitting laser structures in the weak-coupling regime: The cavity/ground-state-exciton resonance," Physical Review B, 59:4, 2894-2901, Jan. 15, 1999.

Miller et al., "Large room-temperature optical nonlinearity in $GaAs/Ga_{1-x}Al_xas$ multiple quantum well structures," Appl. Phys. Lett., 41:8, 679-681, Oct. 15, 1982.

Pollak et al., "Room temperatures, contactless electromodulation investigation of wafer-sized quantum well laser structure," SPIE 2693, 455-466, 1996.

Seraphin et al., "Franz-keldysh effect above the fundamental edge in germanium," Physical Review Letters, 14:5, 138-140, Feb. 1, 1965.

Shay, "Photoreflectance line shape at the fundamental eduge in ultrapure GaAs," Physical Review B, 2:4, 803-807, Aug. 15, 1970.

Weiner et al., "Strong polarization-sensitive electroabsorption in GaAs/AlGaAs quantum well waveguides," Appl. Phys. Lett., 47:11, 1148-1150, Dec. 1, 1985.

Zheng et al., "Photoreflectance and the seraphin coefficients in quantum well structures," SPIE, 946,43-47, 1988.

International Search Report, Dec. 4, 2007.

* cited by examiner

METHOD OF PHOTO-REFLECTANCE CHARACTERIZATION OF STRAIN AND ACTIVE DOPANT IN SEMICONDUCTOR STRUCTURES

CROSS-REFERENCE TO RELATED APPLICATIONS

The present invention claims benefit of U.S. Provisional Patent Application Ser. No. 60/730,293, filed on Oct. 27, 2005, and U.S. Provisional Patent Application Ser. No. 60/831,363, filed on Jul. 17, 2006, which are incorporated herein in their entireties by reference.

FIELD OF THE INVENTION

The present invention relates to optical characterization of semiconductor structures and, more particularly, to the use of photo-modulated reflectance to characterize strain and active dopant in semiconductor structures.

BACKGROUND OF THE INVENTION

High sensitivity non-destructive measurement techniques are required for process control in the fabrication of electronic devices. In order to attain the earliest possible feedback during production, it is necessary to characterize electronic properties before the device is complete. Importantly, the physical phenomena which governs device operation occurs in ultra thin active layers which are difficult to characterize due to their small volume. For example, advanced transistor structures may comprise a thin strained silicon layer, wherein the electrical properties of the transistor are controlled by straining of the silicon lattice. Conventional metrology techniques such as ellipsometry cannot effectively characterize the electronic properties of such thin films. Fortunately, an optical technique known as photo-reflectance may be used to characterize the electronic properties of thin films. The conventional photo-reflectance configuration employs an amplitude modulated laser pump beam to induce small periodic changes in electron-hole population in the thin film of interest. A second optical beam, coincident with the modulated pump beam is then used to monitor small sample reflectivity changes using phase locked detection. This disclosure describes the application of a new photo-reflectance metrology technique to characterize active electronic properties of nanometer thickness silicon films.

The method of photo-reflectance characterization of strain and active dopant in semiconductor structures disclosed herein attains sensitivity to electronic properties of Si nano-filmstructures by using a probe wavelength which is near the first strong interband transition energy in Si, which occurs at a wavelength of approximately 375 nm. In the vicinity of such a transition the photo-reflectance (PR) signal typically will exhibit a sharp derivative-like shape. Generally, the PR signal takes the form $\Delta R/R = \alpha \Delta \epsilon_1 + \beta \Delta \epsilon_2$, where $\alpha$ and $\beta$ are the "Seraphin coefficients" which contain filmstack information, and $\Delta \epsilon_1$ and $\Delta \epsilon_2$, are the pump induced changes in the real and imaginary parts of the dielectric function, respectively (Seraphin, 1965). In other words, $\Delta \epsilon_1$ and $\Delta \epsilon_2$ describe the pump induced modulation of thin film properties. These induced changes may be written as the product of the energy of the free carrier and a third derivative of the semiconductor dielectric function as follows: $\Delta \epsilon_i = \partial^3(\omega \epsilon_i)/\partial \omega^3 \times U_P$, where $U_p$ is the free carrier energy and $\omega$ is the photon frequency (Aspnes, 1980). Thus, the motivation for choosing the wavelength of the probe beam at 375 nm for Si lies in the sharp derivative form for $\Delta \epsilon_1$ and $\Delta \epsilon_2$. This third derivative term may be calculated directly from known semiconductor optical constants. The total PR signal therefore becomes $\Delta R/R = Re[(\alpha - i\beta) \times \partial^3(\omega \epsilon)/\partial \omega^3] \times U_P$. The third derivative functional form is large only nearby strong optical absorptions in the semiconductor band structure, and thus may isolate these features with great precision. This is what allows the PR technique to precisely measure strain in nanoscale strained silicon layers, for example, since the strong optical absorption in Si near 375 nm undergoes a precise shift under strain. Nearby to these strong optical absorptions, the amplitude of the PR response also has excellent sensitivity to electric fields in activated silicon transistor channel regions: note he free electron energy is given by the expression $U_P = e^2 h^2 F^2 / 24 m \omega^2$, where e is the electronic charge, h is Plank's constant, F is the space charge field, and m is the electronic effective mass. This free electron energy is also proportional to the induced carrier density, which may be seen from the Poisson relation: $N_e = \epsilon_o F^2/2$ eV, where $N_e$ is the induced carrier density, V is the built-in surface voltage and $\epsilon_o$ is the permittivity of the material (Shen, 1990).

A primary problem with common commercial photo-reflectometers is the wavelength of the probe beam is not selected to coincide with strong optical absorptions in the electronic material under investigation (Salnick, 2003; Borden, 2000). Thus, in conventional photo-reflectometers, the PR signal is obtained at wavelengths where the third derivative of the dielectric function is small and therefore no information about band structure is available. Thus, conventional photo-reflectometers cannot usefully determine internal electric fields or strain. Rather, these photo-reflectometers are sensitive to the damage profile of implanted dopant (Salnick, 2003). This filmstack information contained in the PR signal is of secondary importance, and produces a cosine-like curve in the PR response as a function of implant depth. Furthermore, implant depth dependence cannot be decoupled from the implant dose dependence in these conventional photo-reflectometers. In any event, the filmstack information provided by conventional commercial photo-reflectometers is available through standard linear optical techniques such as spectroscopic ellipsometry (Jellison, 1995).

A further problem with conventional photo-reflectometers that do employ a lamp based spectroscopic probe beam with wavelengths in the vicinity of strong optical transitions, is that when using such a beam, they must either i) use a monochromer for sequential phase locked measurements at each desired wavelength, or ii) use multiple phase locked detection circuits operating in parallel with a linear photodiode detection array. In the case of use of a monochromer, the total single point measurement time is typically on the order of 5-10 minutes, which is not satisfactory for use in volume manufacturing. In the case of use of parallel phase locked circuits, the cost and complexity of the apparatus are maximized. Moreover, in conventional photo-reflectometers that employ such a lamp based spectroscopic probe beam, the lamp provides incoherent light and hence cannot be focused to a small spot as effectively as a laser beam. In the method of photo-reflectance characterization of strain and active dopant in semiconductor structures disclosed herein all of these problems are solved in an elegant manner. First, the use of a monochromer is unnecessary because the laser probe wavelength is either preset at a known wavelength of interest, or is rapidly scanned over a multiplicity of such known wavelengths. Second, parallel phase locked circuits are unnecessary because only one detection photodiode is required. And finally, the use of a laser source allows tight focusing and rapid data acquisition in accord with process control requirements for volume manufacturing.

An additional problem with common commercial photo-reflectometers is the wavelength of the pump beam is not selected to provide an absorption depth suitable for effective pumping of insulating substrates commonly used in semiconductor manufacturing. For example, in order to effectively pump silicon-on-insulator substrates, the pump laser wavelength is constrained by the requirement the absorption depth be less than or commensurate with the top silicon thickness. This implies suitable pump wavelengths of less than approximately 500 nm, a condition which is not satisfied by common commercial photo-reflectometers (Salnick, 2003).

Thus, while conventional photo-reflectometers/spectrometers may be suitable for the particular purpose to which they address, they are not as suitable as is this disclosure for the characterization of active electronic properties of semiconductor nanostructures before the device is complete.

In these respects, the method of photo-reflectance characterization of strain and active dopant in semiconductor structures disclosed herein substantially departs from the conventional concepts and designs of the prior art, and in so doing, provides an apparatus primarily developed for the rapid characterization of active electronic properties of semiconductor nanostructures in volume manufacturing.

SUMMARY OF THE INVENTION

In view of the foregoing disadvantages inherent in the known types of optical spectroscopy now present in the prior art, the present disclosure provides a new method of photo-reflectance characterization of strain and active dopant in semiconductor structures.

The general purpose of the present disclosure, which will be described subsequently in greater detail, is to provide a method of photo-reflectance characterization of strain and active dopant in semiconductor structures that has many of the advantages of the optical spectroscopy mentioned heretofore and many novel features that result in a method of photo-reflectance characterization of strain and active dopant in semiconductor structures which is not anticipated, rendered obvious, suggested, or implied by any of the prior art, either alone or in any combination thereof.

The underlying principle of the strain characterization technique is to measure small wavelength shifts in photo-reflectance signals occurring near strong interband transitions in the semiconductor bandstructure. The position of the PR peaks allows direct determination of thin film physical properties such as strain. The underlying principle of the active dopant characterization technique is likewise to measure photo-reflectance signals occurring near strong interband transitions in the semiconductor bandstructure, and which are highly sensitive to activated dopant through the effect of the nanometer scale space charge fields induced at the semiconductor surface. The PR signal allows direct determination of thin film physical properties such as active doping concentration. Thus, the method of photo-reflectance characterization of strain and active dopant in semiconductor structures provides the ability to generate and record photo-reflectance information relating to active electronic properties of semiconductor nanostructures.

To attain this, the present disclosure comprises, as one potential embodiment, a diode laser pump beam of approximately 15 mW operating in the NIR-VIS. The pump beam is amplitude modulated by a signal generator operating in the range of 100 kHz-50 MHz. The pump laser may be modulated directly or the pump beam may be modulated through conventional electro-optic or acousto-optic modulation techniques. The pump polarization may be varied by fixturing a polarizer. The probe beam comprises, as one potential embodiment, a diode laser beam of approximately 5 mW operating in the VIS-UV. The pump and probe are made collinear by use of a dichroic beamsplitter. The collinear pump and probe are directed to a micrometer scale spot on the sample and specular reflections are collected. The pump light is then attenuated using a color filter and the remaining probe light, containing the modulated reflectivity of the sample, is then focused into the photodiode and converted to electric current. This current is passed to the lock-in amplifier which measures the amplitude and phase of the reflectivity change. This PR signal is then stored as function of probe wavelength, pump intensity, and pump and probe polarizations. Thus photo-reflectance information related to the active electronic properties of semiconductor nanostructures is acquired.

The semiconductor materials that are the subject of the present disclosure may be any semiconductor materials, and may include, but are not limited to Group II-VI semiconductor materials or Group III-V semiconductor materials. In certain embodiments such materials may include silicon, carbon, germanium, silicon carbide, silicon germanium, boron, phosphorus, arsenic, or any combinations thereof, or they may include gallium arsenide, aluminum arsenide, gallium nitride, aluminum nitride, indium nitride, gallium phosphide, indium phosphide, indium arsenide, or any combinations thereof.

There has thus been outlined, rather broadly, the more important features of the disclosure in order that the detailed description thereof may be better understood, and in order that the present contribution to the art may be better appreciated. There are additional features of the disclosure that will be described hereinafter.

In this respect, before explaining at least one embodiment of the disclosure in detail, it is to be understood that the disclosure is not limited in its application to the details of construction and to the arrangements of the components set forth in the following description or illustrated in the drawings. The disclosure is capable of other embodiments and of being practiced and carried out in various ways. Also, it is to be understood that the phraseology and terminology employed herein are for the purpose of the description and should not be regarded as limiting. This disclosure may be embodied in the form illustrated in the accompanying drawings, attention being called to the fact, however, that the drawings are illustrative only, and that changes may be made in the specific construction illustrated.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

DETAILED DESCRIPTION

The following discusses use of the method of photo-reflectance characterization of strain and active dopant in semiconductor structures for characterization of strain and active dopant in silicon nanofilmstructures. It is understood that the method of photo-reflectance characterization of strain and active dopant in semiconductor structures of the present disclosure may be used to analyze any semiconductor structure, the discussion of silicon nanofilmstructures considered to be exemplary only and in no way limiting in scope.

Figure 1:
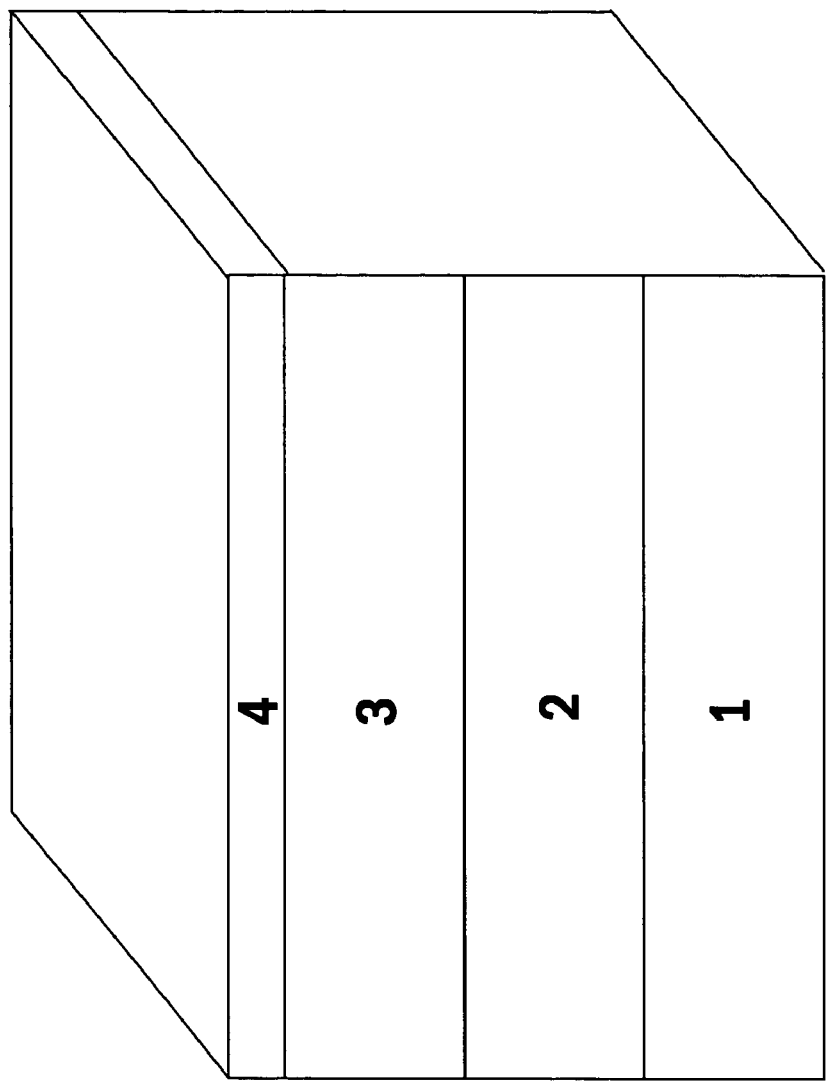
FIG. 1 illustrates an exemplary strained silicon filmstructure that may be analyzed using the strain characterization technique of the present disclosure.

Turning now descriptively to the drawings, FIG. 1 contains, in an exaggerated view, an exemplary strained silicon filmstructure that may be characterized using the photo-reflectance technique of the present disclosure. Strained silicon filmstructure, which may be grown using molecular beam epitaxy, and/or chemical vapor deposition, and/or metal-organic chemical vapor deposition, comprises a silicon substrate 1 upon which is grown a graded composition silicon germanium layer 2 of increasing Ge content (up to approximately 10-30% Ge), followed by a uniform composition SiGe layer 3, and finally a top thin strained silicon film 4. The SiGe layers 2 and 3 form a virtual SiGe substrate to which the top silicon lattice conforms, thereby inducing tensile strain in the top silicon layer. In an exemplary embodiment, the top strained Si layer 4 comprises a thickness of approximately 10.0 nm.

Figure 2:
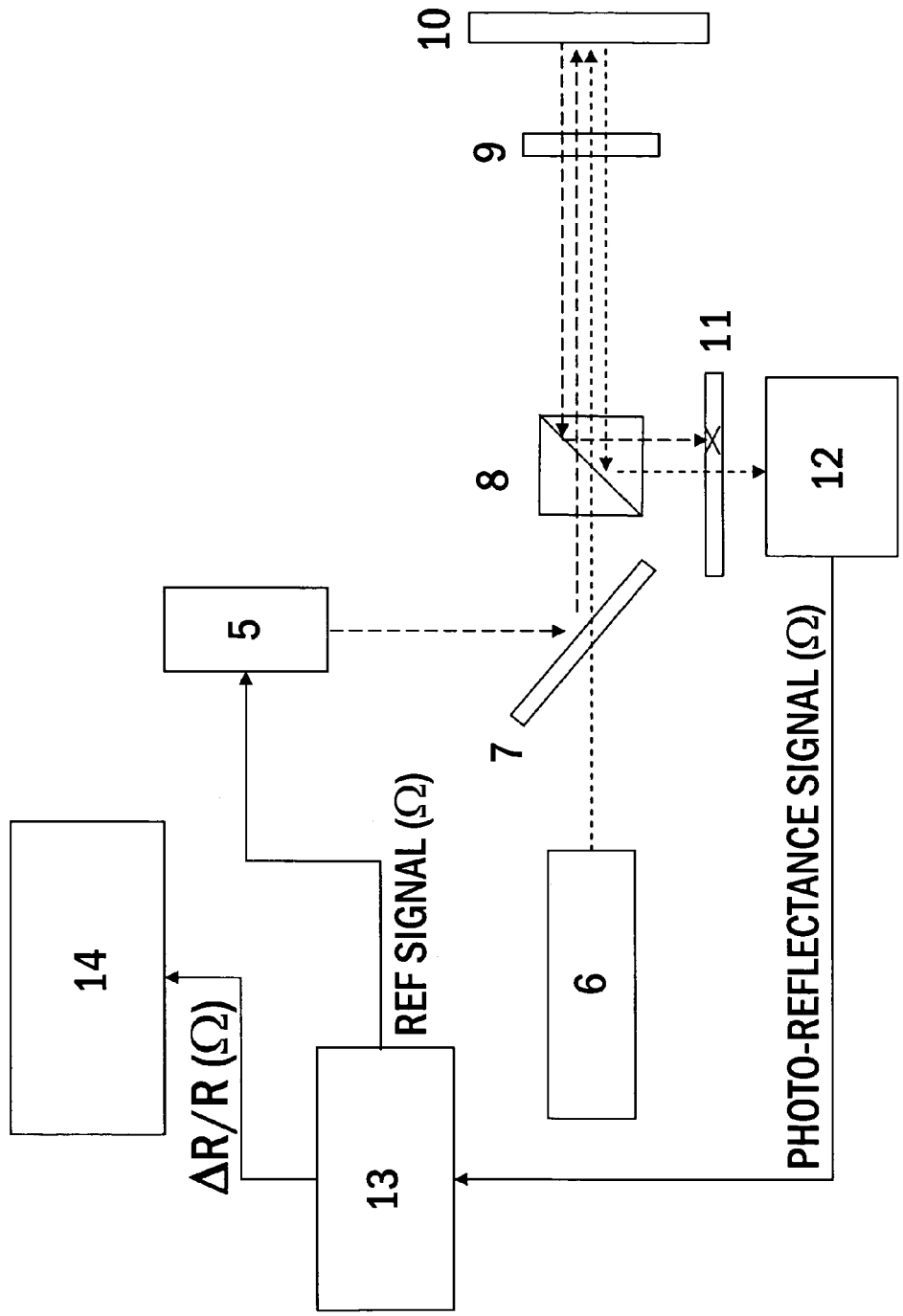
FIG. 2 contains an arrangement of the photo-reflectivity apparatus which may be used to provide photo-reflectance characterization of strain and active dopant in semiconductor structures in accordance with present disclosure.

In accordance with the arrangement of the present disclosure as shown in FIG. 2, the method of photo-reflectance characterization of strain and active dopant in semiconductor structures may be used to measure the reflected spectra from the strained silicon nanofilmstructure, or any other semiconductor structure, in order to characterize the physical properties of the semiconductor structure such as the energy of interband transitions, the active carrier concentration, and the surface electric field. As shown in FIG. 2, said photo-reflectance arrangement comprises a pump laser 5, a probe laser 6, a dichroic beamsplitter 7, a polarizing beamsplitter 8, an achromatic quarter-wave plate 9, a reflecting sample 10, a color filter 11, a photodiode 12, a lock-in amplifier 13, and a computer 14 to control measurement parameters and record reflectivity changes. In an exemplary embodiment, the pump laser intensity is directly modulated using a 1 volt peak to peak square wave reference signal from the lock-in amplifier 13. The pump and probe beams are made collinear through the use of the dichroic beamsplitter 7. The collinear beams are then focused onto the reflecting sample 10 using an achromatic focusing lens, and collected using a collection lens. The pump light is then attenuated using a color filter 11. The remaining probe light, containing the modulated reflectivity of the sample, is then focused into the photodiode 12 and converted to electric current. This current is passed to the lock-in amplifier 13 which measures the amplitude and phase of the reflectivity change. This information is passed to the computer 14 which records the differential change in reflectivity as a function of driving frequency.

Figure 3:
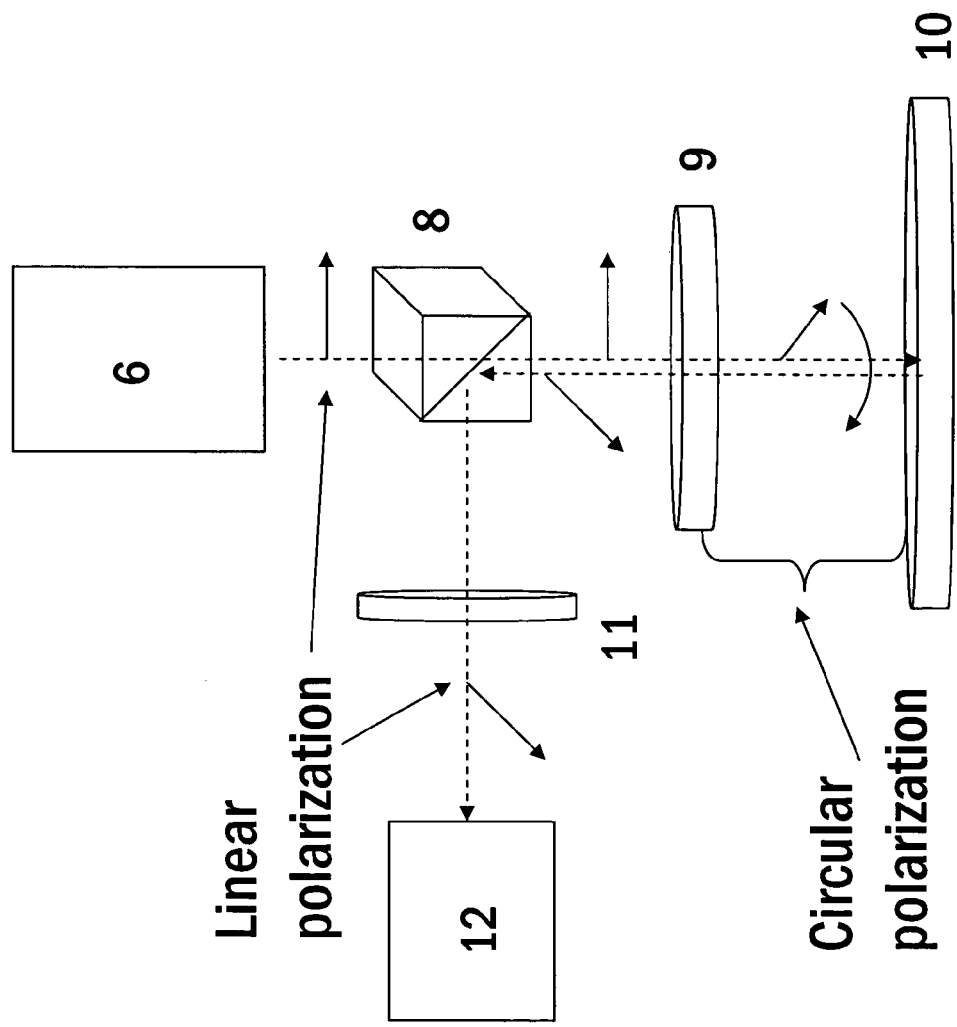
FIG. 3 contains a schematic arrangement of the photo-reflectivity apparatus probe beam polarization which may be used to provide photo-reflectance characterization of strain and active dopant in semiconductor structures in accordance with present disclosure.

The pump laser 5 is a continuous wave laser with photon energy at or above the band gap of the semiconductor under investigation. For silicon, the band gap occurs at approximately 1100 nm wavelength. In an exemplary embodiment, the pump wavelength is approximately 488 nm and the pump laser power is approximately 15 mW. This wavelength is particularly useful when the active layer is the thin top silicon layer of a silicon-on-insulator substrate such that the pump light must be absorbed within the top Si layer to effectively modulate the carrier density. The pump laser intensity may be controlled by the computer 14. Pump laser 5 embodiments include diode lasers emitting in the NIR-VIS wavelength range operating at powers of approximately 5 mW or above. The pump laser beam may be directly modulated or modulated externally through use of an electro-optic or acousto-optic amplitude modulation arrangement. In an exemplary embodiment, the pump laser 5 is directly modulated at high frequency by the internal reference signal from the lock-in amplifier 13. The driving frequency varies from approximately 100 kHz to 50 MHz. The pump laser beam may also be passed through a polarizer whose angular position may be controlled by the computer. This provides an amplitude modulated, variable polarization, pump beam. The probe laser 6 comprises a continuous wave laser diode with photon energy at or near an interband transition energy of the semiconductor under investigation. For silicon, the first strong interband absorption occurs at approximately 375 nm wavelength. In an exemplary embodiment, the probe wavelength is approximately 375 nm and the probe laser power is approximately 5 mW. In certain embodiments the probe laser 6 is an external cavity tunable diode laser with center wavelength of approximately 375 nm and tunable range of approximately 10 nanometers, or greater. Probe laser 6 embodiments include diode lasers emitting in the VIS-UV wavelength range operating at powers of approximately 10 mW or less. The pump and probe beams are made collinear through the use a dichroic beamsplitter 7. The collinear beams are focused onto the sample using a high numerical aperture focusing arrangement, and the specular reflections are collected and directed onto a color filter 11. Focusing embodiments include coincident beam arrangements wherein either laser beam is focused to a diameter of 50 microns or less. FIG. 3 schematically shows the probe laser beam and polarization as it passes through the optical system. All optical elements are matched to the respective source wavelength. Once the probe beam is reflected from the reflecting sample 10, it has an amplitude modulation at the pump modulation frequency from the induced modulation of sample optical properties. Thus, the probe beam contains a signal of the form $I_o[R(DC)+\Delta R(\Omega)]$. Light from the pump beam is attenuated with the color filter 11 and the remaining probe light is passed to the photodiode 12. Thus, the photodiode output contains electrical currents proportional to the probe signal.

The DC signal from the photodiode is proportional to $I_o R$, while the AC signal is proportional to $I_o \Delta R$. In order to measure $\Delta R/R$, the intensity $I_o$ must be normalized. This is accomplished by dividing the AC signal by the DC signal. Typical amplitudes of $\Delta R/R$ for the exemplary embodiment are on the order $10^{-2}$-$10^{-6}$. Phase sensitive measurement is performed on the photodiode output and the computer 14 records the measurement photocurrents. The computer 14 may control the probe wavelength, the modulation frequency, the pump laser intensity, and polarization of either beam. Thus $\Delta R/R$ is recorded as a function of probe wavelength, modulation frequency, laser intensity and polarization. Embodiments include alterations to the arrangement which do not alter the fundamental PR signal.

Figure 4:
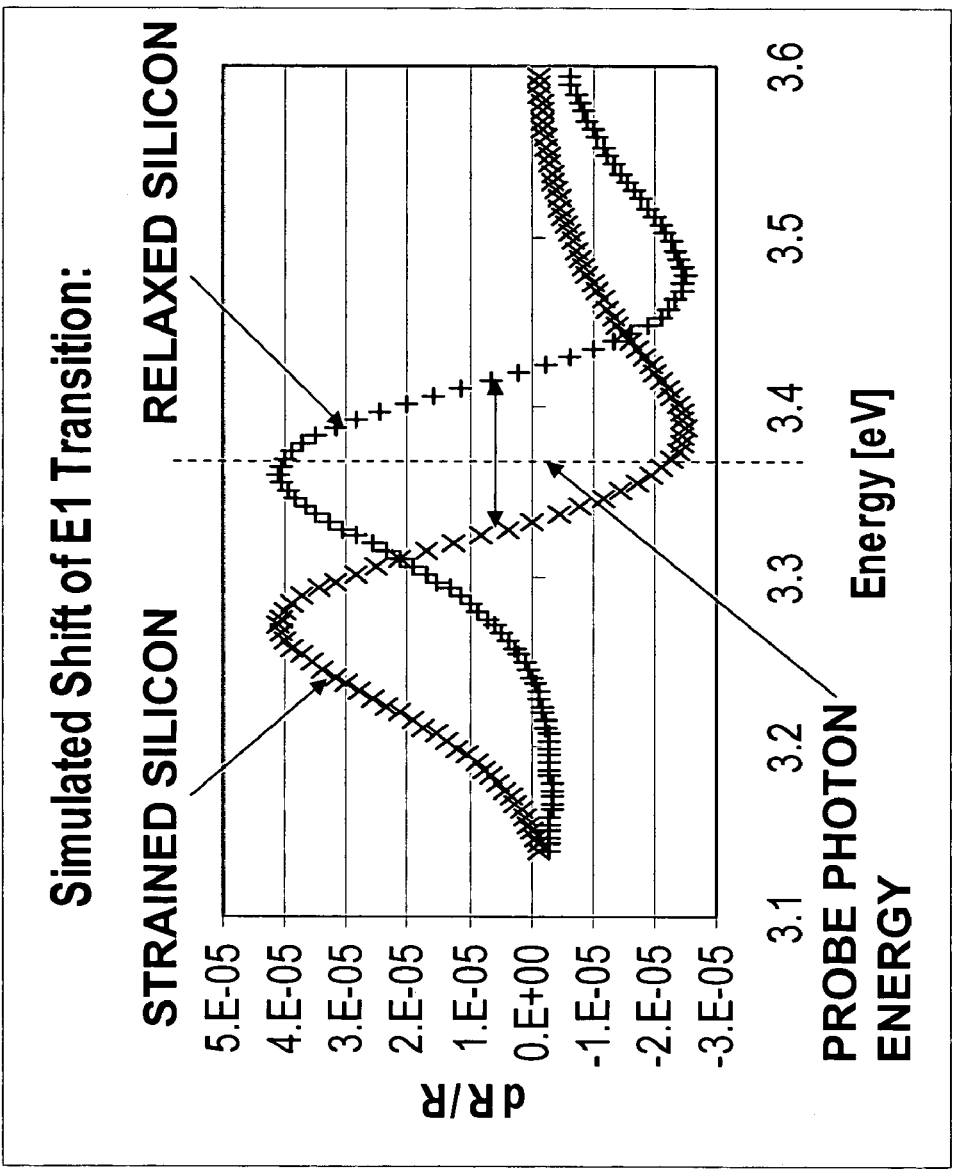
FIG. 4 contains a schematic shift of the "$E_1$" interband transition in silicon due to biaxial strain and illustrates the principle of measurement of the strain characterization technique of the present disclosure.

As mentioned, the underlying principle of the strain characterization technique is to measure small shifts in photoreflectance signals occurring near strong interband transitions in the semiconductor bandstructure. FIG. 4. illustrates the underlying principle for monitoring strain in thin strained silicon films using a single probe wavelength. The silicon "$E_1$" interband transition occurring at $\lambda \cong 375$ nm is known to undergo a split and shift under strain. The positions of the strained interband transition energies are given by: $E_\pm = E_1 + \Delta E_H \pm \Delta E_S$, where $\Delta E_H$ (<0) and $\Delta E_S$ correspond to the hydrostatic and shear induced shifts, respectively. These terms are both linear in strain, leading to an overall shift linearly proportional to strain. FIG. 4 contains simulated PR signals corresponding to the unstrained silicon $E_1$ interband transition energy and the redshifted $E_-$ interband transition energy, for a silicon lattice strain of approximately 1%. As illustrated, for a monochromatic probe beam near the $E_1$ interband transition energy, the PR signal will undergo a sign change in the presence of strain. Thus, by selecting a single probe wavelength at or very near a strong interband transition of the unstrained semiconductor under investigation, the presence of strain may be determined by a change of sign of the PR response. Additionally, as exhibited in FIG. 4, at or very near such an interband transition the PR signal is a linear function of strain. Therefore the PR signal may be used to simply monitor the magnitude of the strain according to an approximate linear equation: $\Delta R/R = m\chi + b$, where $\chi$ is the physical strain, m is an empirically determined linear correlation coefficient, and b is a small offset.

Figure 5:
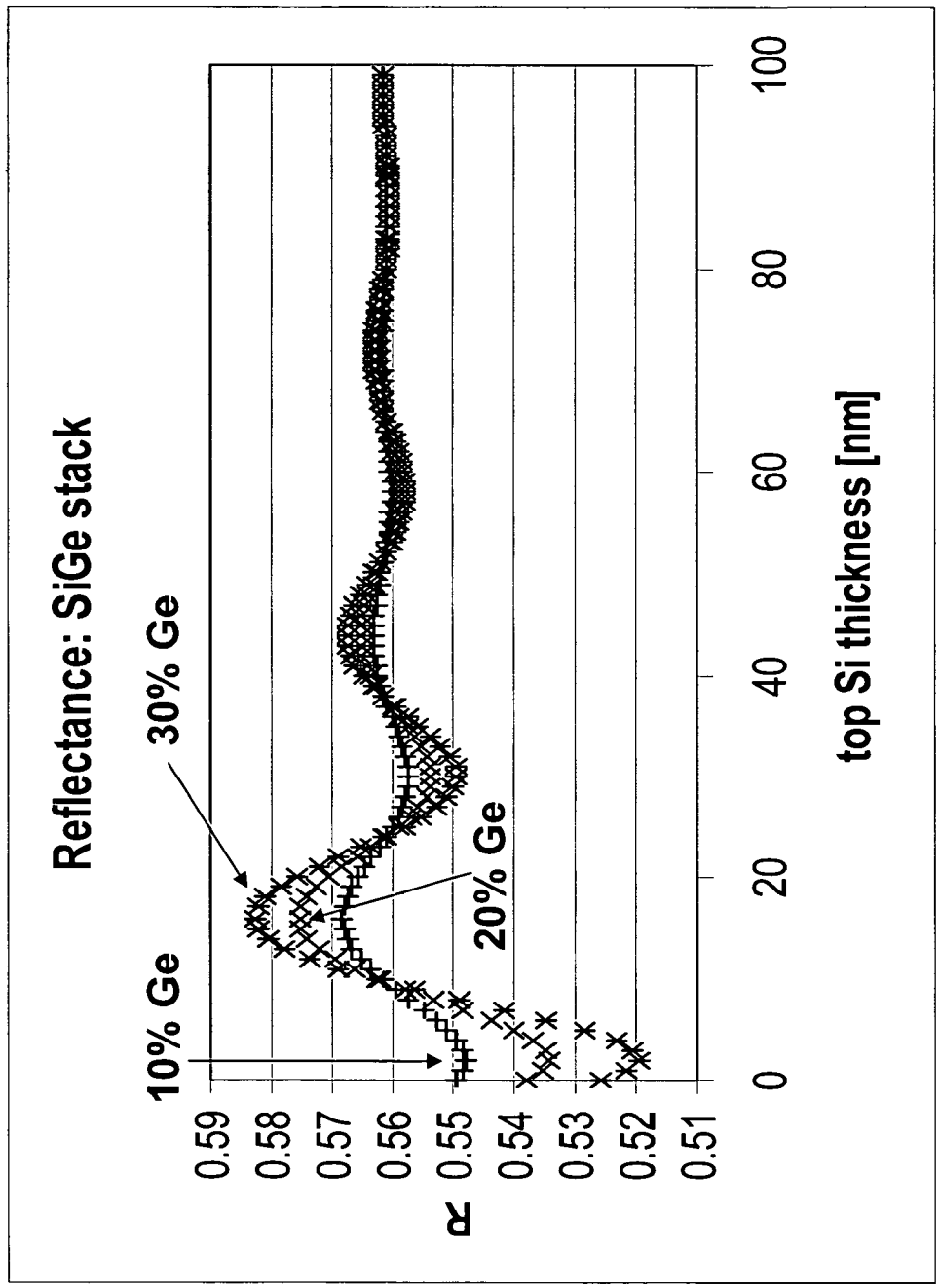
FIG. 5 is the calculated DC reflectance, at $\lambda=375$ nm, of a thin silicon film on top of an optically thick silicon germanium layer as a function of top silicon thickness and SiGe layer Ge concentration.
Figure 6:
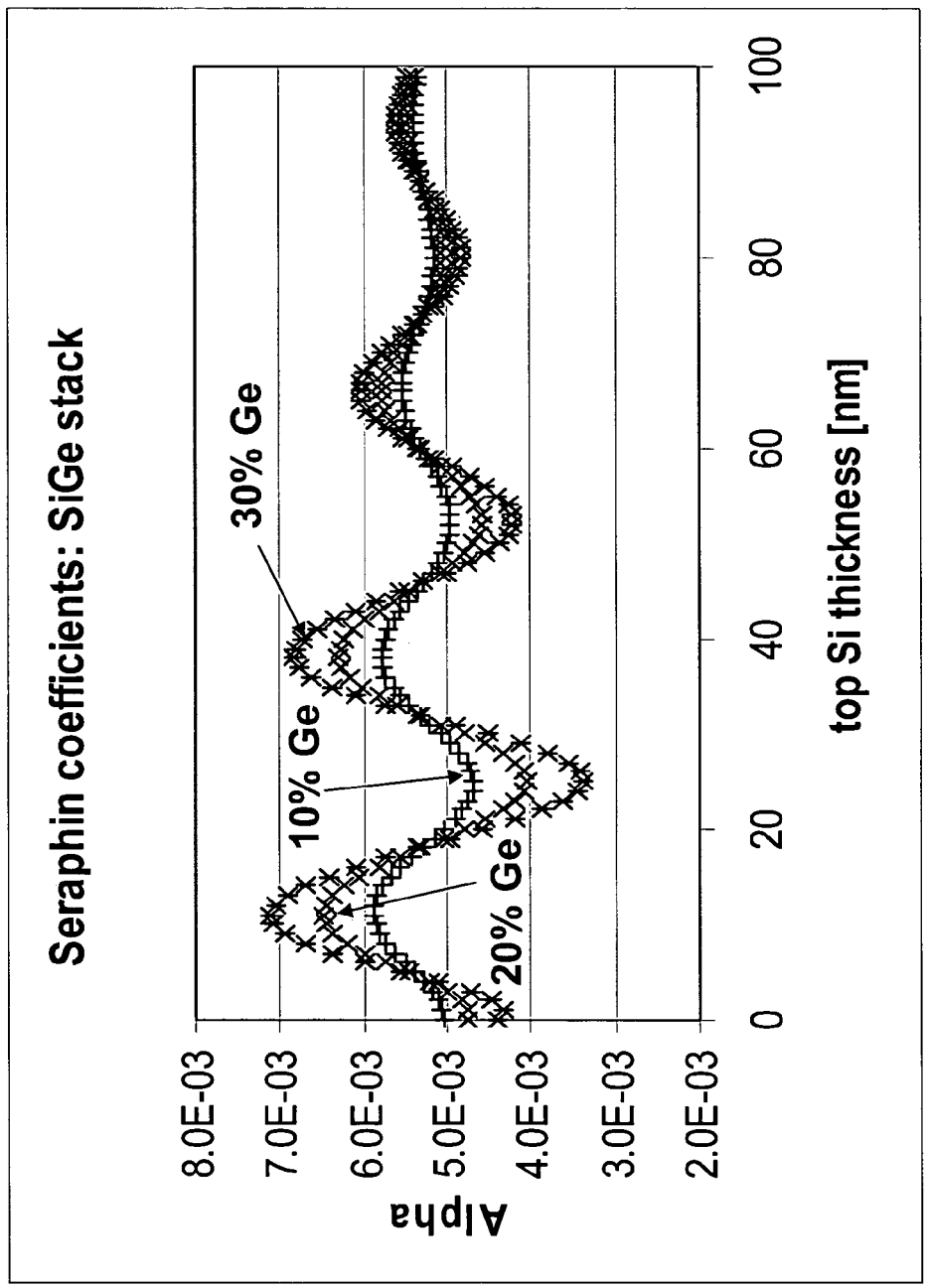
FIG. 6 is the calculated Seraphin coefficient $\alpha=\partial(\ln R)/\partial\in_1$, at $\lambda=375$ nm, of a thin silicon film on an optically thick silicon germanium layer as a function of top silicon thickness and SiGe layer Ge concentration.
Figure 7:
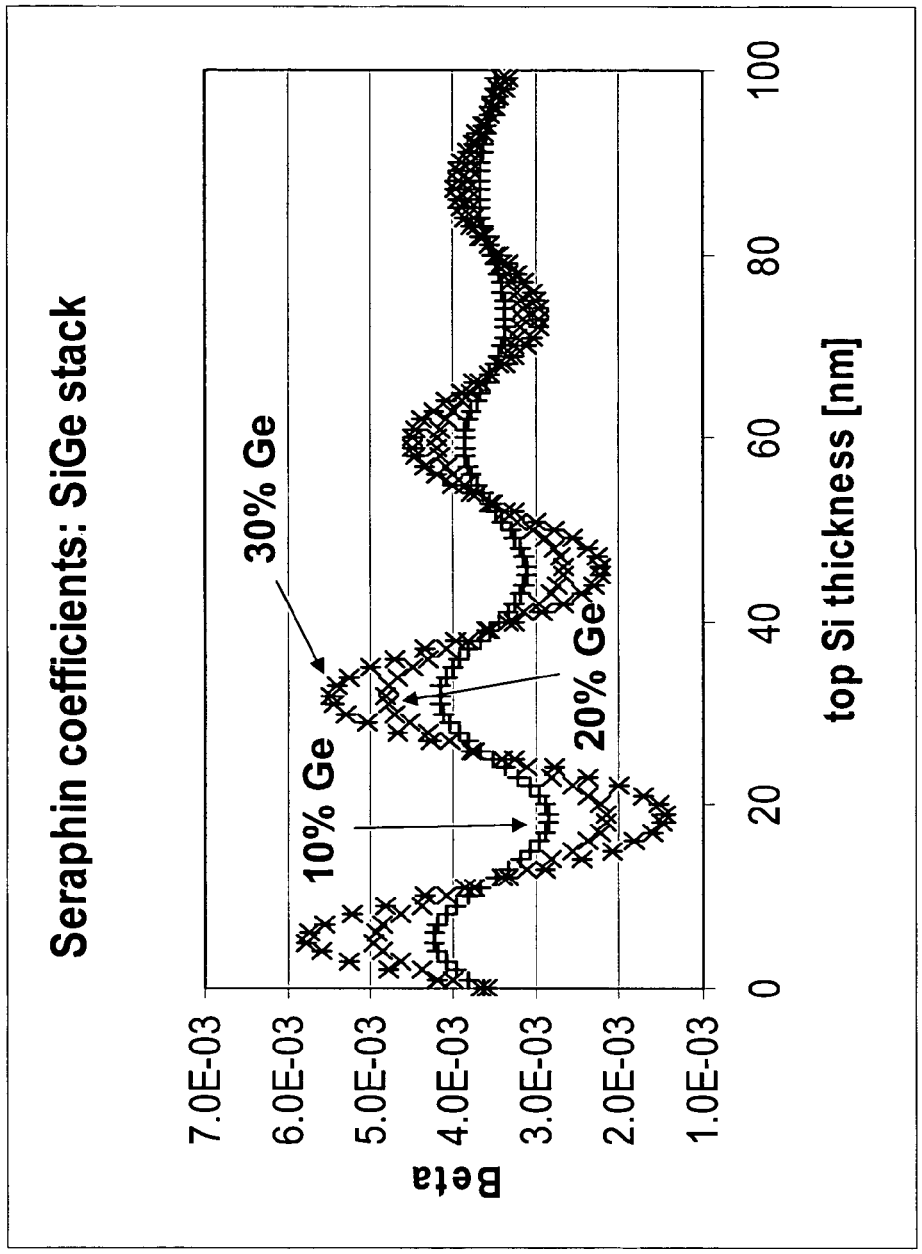
FIG. 7 is the calculated Seraphin coefficient $\beta=\partial(\ln R)/\partial\in_2$, at $\lambda=375$ nm, of a thin silicon film on an optically thick silicon germanium layer as a function of top silicon thickness and SiGe layer Ge concentration.

In correlation of the PR signal $\Delta R/R$ to strain, it is important to know the effect of the filmstack on the PR signal. This is provided by the constitutive relation: $\Delta R/R = \alpha \Delta \in_1 + \beta \Delta \in_2$, where $\alpha$ and $\beta$ are the Seraphin coefficients containing the filmstack information, and $\Delta \in_1$ and $\Delta \in_2$ are the pump induced changes in real and imaginary parts of the sample pseudo-dielectric function, respectively. The absorption depth sets the depth of the PR response and hence the range over which it is important to know the effect of the filmstack on PR signal. At 375 nm wavelength, the absorption depth in silicon is $\delta \cong 22.6$ nm. This means that for top silicon thicknesses greater than 22.6 nm, a 375 nm probe beam rapidly loses sensitivity to underlying film structure. FIG. 5 contains the calculated reflectance of the exemplary film structure shown in FIG. 1, as a function of top silicon thickness, for typical SiGe Ge concentrations of 10%, 20%, and 30%. By numerically differentiating this reflectivity with respect to $\in_1$ and $\in_2$, it is possible to calculate the Seraphin coefficients, i.e: $\alpha = \partial(\ln R)/\partial \in_1$ and $\beta = \partial(\ln R)/\partial \in_2$. FIGS. 6 & 7 contain the Seraphin coefficients for the exemplary film structure shown in FIG. 1, as a function of top silicon thickness, for typical SiGe Ge concentrations of 10%, 20%, and 30%. The fact that the Seraphin coefficients do not change sign over the parameter space of interest demonstrates that any change of sign observed in the PR signal at 375 nm cannot be due to variations in top silicon thickness or Ge concentration. Therefore, any change in sign of $\Delta R/R$ is necessarily due to a change in sign of $\Delta \in_1$ or $\Delta \in_2$, indicating the presence of strain. The calculated Seraphin coefficients also demonstrate the dependence of $\Delta R/R$ on filmstack parameters.

In order to demonstrate the PR signal change associated with the presence of strain two sample sets containing variations of the exemplary structure of FIG. 1 were analyzed. The fundamental question of interest is which, if any, of the top silicon films in each of these sets are strained. Sample set 1 contained five wafers: an unstrained silicon substrate; two wafers with relaxed SiGe (~18.5% Ge) on silicon substrates; and two wafers with relaxed SiGe (~18.5% Ge) on silicon substrates with additional top strained silicon films of approximately 6 nm thickness. Sample set 1 is described in Table 1 below.

TABLE 1

|  | # 1 | # 2 | # 3 | # 4 | # 5 |
|---|---|---|---|---|---|
| Filmstack | Si Subs | Top Si/SiGe/Sub | SiGe/Sub | Top Si/SiGe/Sub | SiGe/Sub |
| % Ge | N/A | ~18.5% | ~18.5% | ~18.5% | ~18.5% |
| Top Si thickness | N/A | ~6 nm | N/A | ~6 nm | N/A |

Sample set 2 contained six wafers—each comprising the full stack of in FIG. 1, with variations in top silicon thickness and Ge concentration. Sample set 2 is described in Table 2 below.

TABLE 2

|  | # 1 | # 2 | # 3 | # 4 | # 5 | # 6 |
|---|---|---|---|---|---|---|
| Filmstack | | | Top Si/SiGe/Substrate | | | |
| % Ge | ~15% | ~20% | ~20% | ~20% | ~15% | ~20% |
| Top Si thickness | ~20 nm | ~10 nm | ~10 nm | ~10 nm | ~20 nm | ~30 nm |

Figure 8:
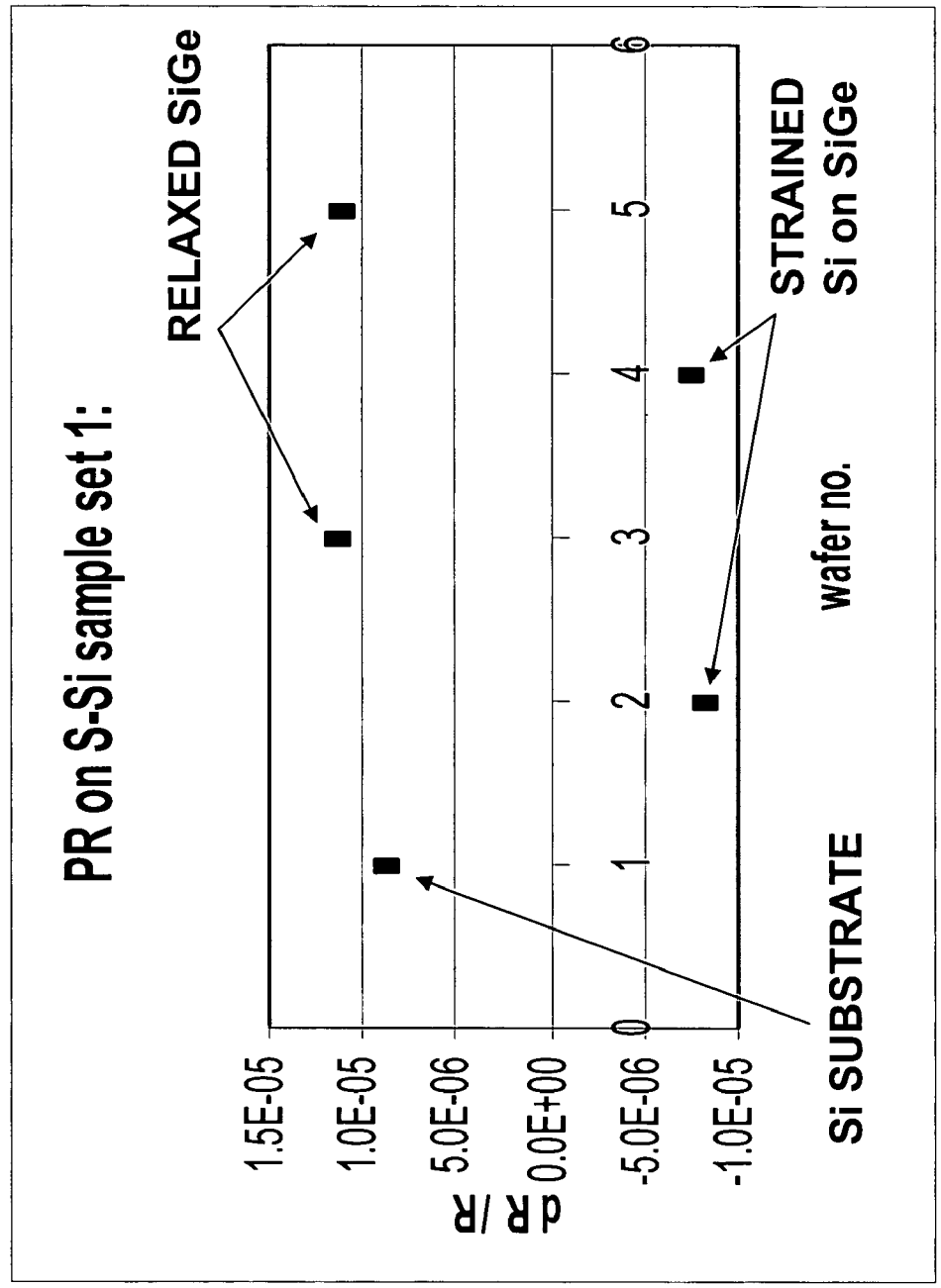
FIG. 8 is the experimental PR signal, at a modulation frequency of 20 MHz, plotted for each sample in sample set 1.

FIG. 8 shows the PR data taken on sample set 1, at a fixed modulation frequency of 20 MHz. Wafers #1, #3, & #5, the unstrained silicon substrate and relaxed SiGe wafers, show PR signals of around $+1 \times 10^{-5}$. Since the PR spectra is a linear superposition of the response from the top silicon film and the relaxed SiGe layers, we can conclude that if wafers #2 and #4 contained unstrained top silicon, the response of these wafers must be positive, similar to wafers #1, #3, and #5. However, wafers #2 and #4, the only wafers with top silicon, show PR signals of opposite sign. Further, as demonstrated in FIGS. 6 & 7, the change of sign of the PR response seen for wafers #2 and #4 cannot be a filmstack effect. Therefore, the negative PR signal seen for wafers #2 and #4 is due to strain in the top silicon, in accordance with the strain measurement principle as depicted in FIG. 4.

Figure 9:
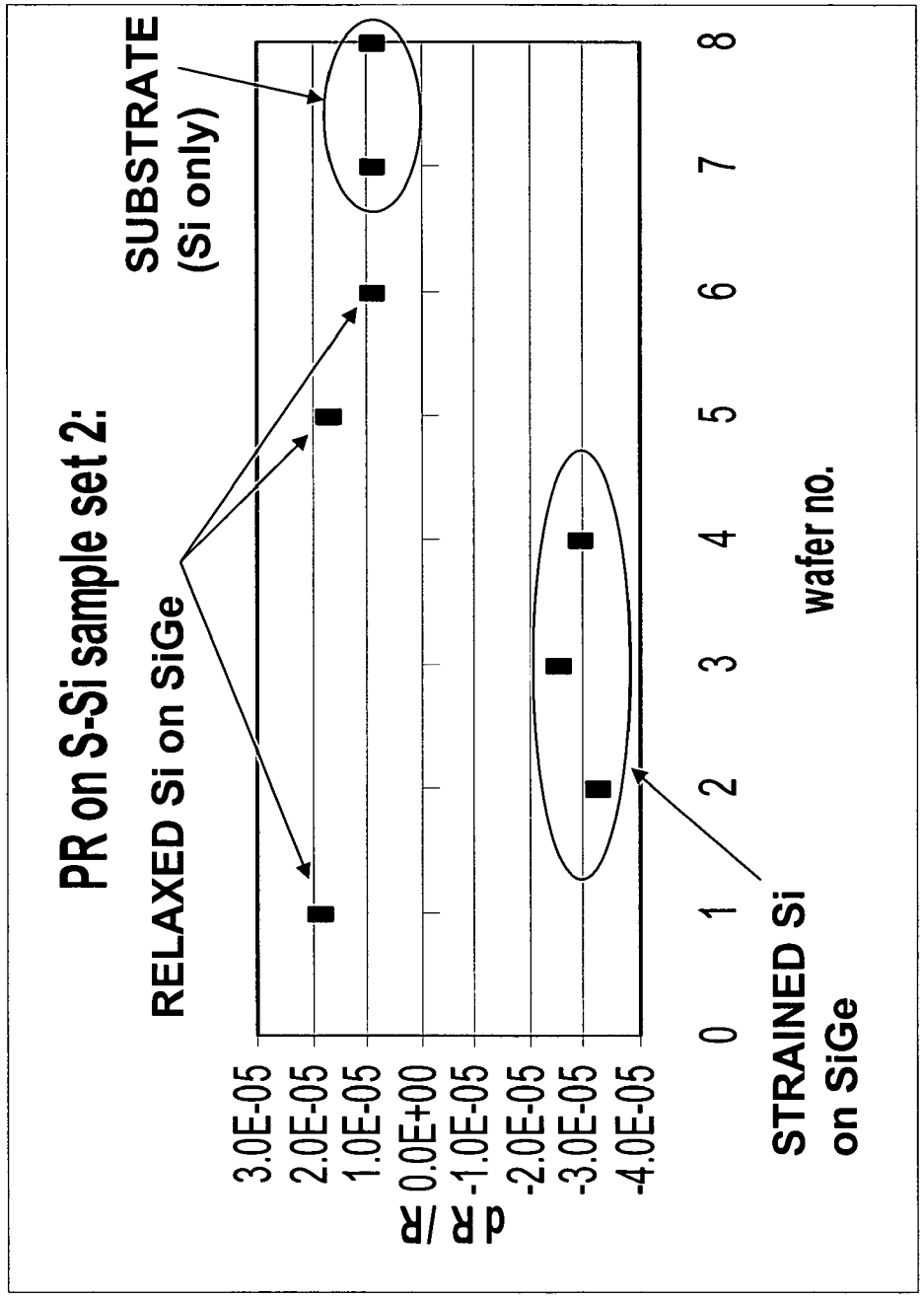
FIG. 9 is the experimental PR signal, at a modulation frequency of 20 MHz, plotted for each sample in sample set 2.

FIG. 9 shows the PR data taken on sample set 2, at a fixed modulation frequency of 20 MHz. Wafers #1, #5, & #6, show PR signals of $\sim 1-2 \times 10^{-5}$. However, wafers #2, #3, and #4 show PR signals of opposite sign and magnitude $\sim 3-4 \times 10^{-5}$. By examination of Table 2, it may be seen the negative PR signals correspond to wafers with top silicon film thicknesses of approximately 10 nm, while the positive signals correspond to films of thickness approximately 20 nm. However, as demonstrated in FIGS. 6 & 7, the negative PR response cannot be a filmstack effect. This shows that on sample set 2, the strain is relaxed when the top silicon thickness exceeds approximately 20 nm. This conclusion is supported by independent calculations predicting strain relaxation for top silicon films thicker than approximately 15 nm thickness (under the conditions herein). In analogy with the results of sample set 1, we conclude that wafers #2, #3, and #4 of sample set 2 are strained, while the others are not.

Figure 10:
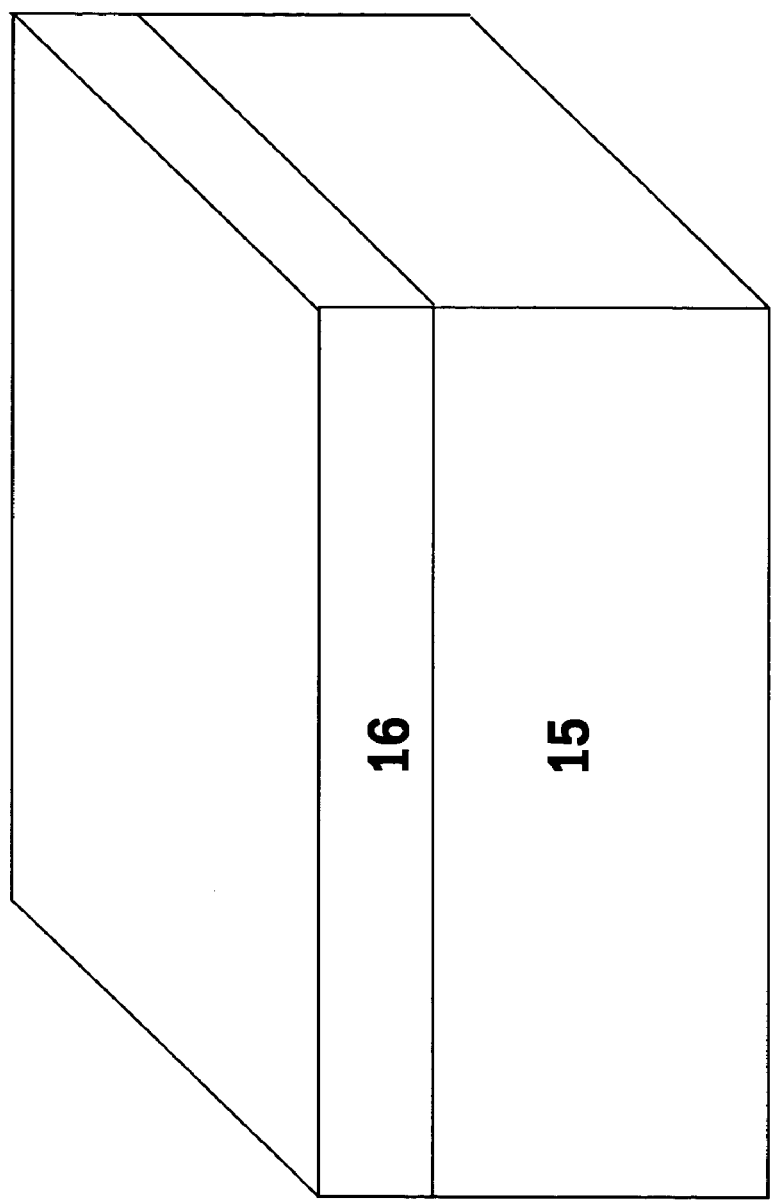
FIG. 10 illustrates an exemplary implanted/annealed silicon nanofilmstructure that may be analyzed using the method of photo-reflectance characterization of active dopant in semiconductor structures of the present disclosure.

Turning now to exposition of the active dopant characterization technique, FIG. 10 contains, in an exemplary view, implanted and annealed silicon filmstructure that may be analyzed using the method of photo-reflectance characterization of strain and active dopant in semiconductor structures of the present disclosure. The implanted and annealed silicon nanofilmstructure comprises a standard silicon substrate 15 used in the manufacture of integrated circuits, into which is implanted a uniform layer of arsenic (As) dopant, and after which is performed an activation anneal. In an exemplary embodiment, the implant layer 16 comprises a thickness of approximately 10-40 nm located at or near the wafer surface. In actuality the implanted dopant forms a graded distribution so FIG. 10 only provides an approximate structure to model the optical properties of the implanted and annealed silicon nanofilmstructure. A set of arsenic implanted silicon wafers with varying implant dose and implant energies was generated. The process matrix used 24 wafers with implant dose and depth targeted to approximate current and future manufacturing specifications. The implanted energies were varied to produce depths in the range of approximately 10 nm to 40 nm, while the doses were varied to produce nominal doping densities of approximately $10^{18}$ atoms/cc to $10^{20}$ atoms/cc. Annealed and non-annealed wafers were created for each implant split. Table 3 contains information on the matrix, including estimated doping profiles. There are 4 implant energies: wafer #'s 1-6, 7-12, 13-18, and 19-24 correspond to implanted depths of 10, 20, 30, and 40 nm, respectively. Each of these target depths further comprises three dose splits on the order of $10^{12}$, $10^{13}$, and $10^{14}$ ions per square cm. The lightest dose corresponds to a density of roughly $1 \times 10^{18}$ ions/cc. Finally, an anneal split was performed comprising a single anneal of 5 seconds at 1000° C. This anneal is intended to result in maximal dopant activation for all dose and density conditions. No attempt to minimize dopant diffusion was made.

TABLE 3

| Wafer No. | Implant Energy | Target depth [nm] | Straggle [nm] | Dose [1/cm^2] | Density [1/cc] | Anneal condition |
|---|---|---|---|---|---|---|
| 1 | 7 keV | 10.2 | 3.6 | 1.00E+12 | 9.80E+17 | XX |
| 2 | 7 keV | 10.2 | 3.6 | 1.00E+12 | 9.80E+17 | 5 s at 1000° C. |
| 3 | 7 keV | 10.2 | 3.6 | 1.00E+13 | 9.80E+18 | XX |
| 4 | 7 keV | 10.2 | 3.6 | 1.00E+13 | 9.80E+18 | 5 s at 1000° C. |
| 5 | 7 keV | 10.2 | 3.6 | 1.00E+14 | 9.80E+19 | XX |
| 6 | 7 keV | 10.2 | 3.6 | 1.00E+14 | 9.80E+19 | 5 s at 1000° C. |
| 7 | 20 keV | 20.3 | 7.2 | 2.00E+12 | 9.85E+17 | XX |
| 8 | 20 keV | 20.3 | 7.2 | 2.00E+12 | 9.85E+17 | 5 s at 1000° C. |
| 9 | 20 keV | 20.3 | 7.2 | 2.00E+13 | 9.85E+18 | XX |
| 10 | 20 keV | 20.3 | 7.2 | 2.00E+13 | 9.85E+18 | 5 s at 1000° C. |
| 11 | 20 keV | 20.3 | 7.2 | 2.00E+14 | 9.85E+19 | XX |
| 12 | 20 keV | 20.3 | 7.2 | 2.00E+14 | 9.85E+19 | 5 s at 1000° C. |
| 13 | 35 keV | 30.6 | 10.8 | 3.00E+12 | 9.80E+17 | XX |
| 14 | 35 keV | 30.6 | 10.8 | 3.00E+12 | 9.80E+17 | 5 s at 1000° C. |
| 15 | 35 keV | 30.6 | 10.8 | 3.00E+13 | 9.80E+18 | XX |
| 16 | 35 keV | 30.6 | 10.8 | 3.00E+13 | 9.80E+18 | 5 s at 1000° C. |

TABLE 3-continued

| Wafer No. | Implant Energy | Target depth [nm] | Straggle [nm] | Dose [1/cm^2] | Density [1/cc] | Anneal condition |
|---|---|---|---|---|---|---|
| 17 | 35 keV | 30.6 | 10.8 | 3.00E+14 | 9.80E+19 | XX |
| 18 | 35 keV | 30.6 | 10.8 | 3.00E+14 | 9.80E+19 | 5 s at 1000° C. |
| 19 | 50 keV | 40.6 | 13.9 | 4.00E+12 | 9.85E+17 | XX |
| 20 | 50 keV | 40.6 | 13.9 | 4.00E+12 | 9.85E+17 | 5 s at 1000° C. |
| 21 | 50 keV | 40.6 | 13.9 | 4.00E+13 | 9.85E+18 | XX |
| 22 | 50 keV | 40.6 | 13.9 | 4.00E+13 | 9.85E+18 | 5 s at 1000° C. |
| 23 | 50 keV | 40.6 | 13.9 | 4.00E+14 | 9.85E+19 | XX |
| 24 | 50 keV | 40.6 | 13.9 | 4.00E+14 | 9.85E+19 | 5 s at 1000° C. |

Figure 11:
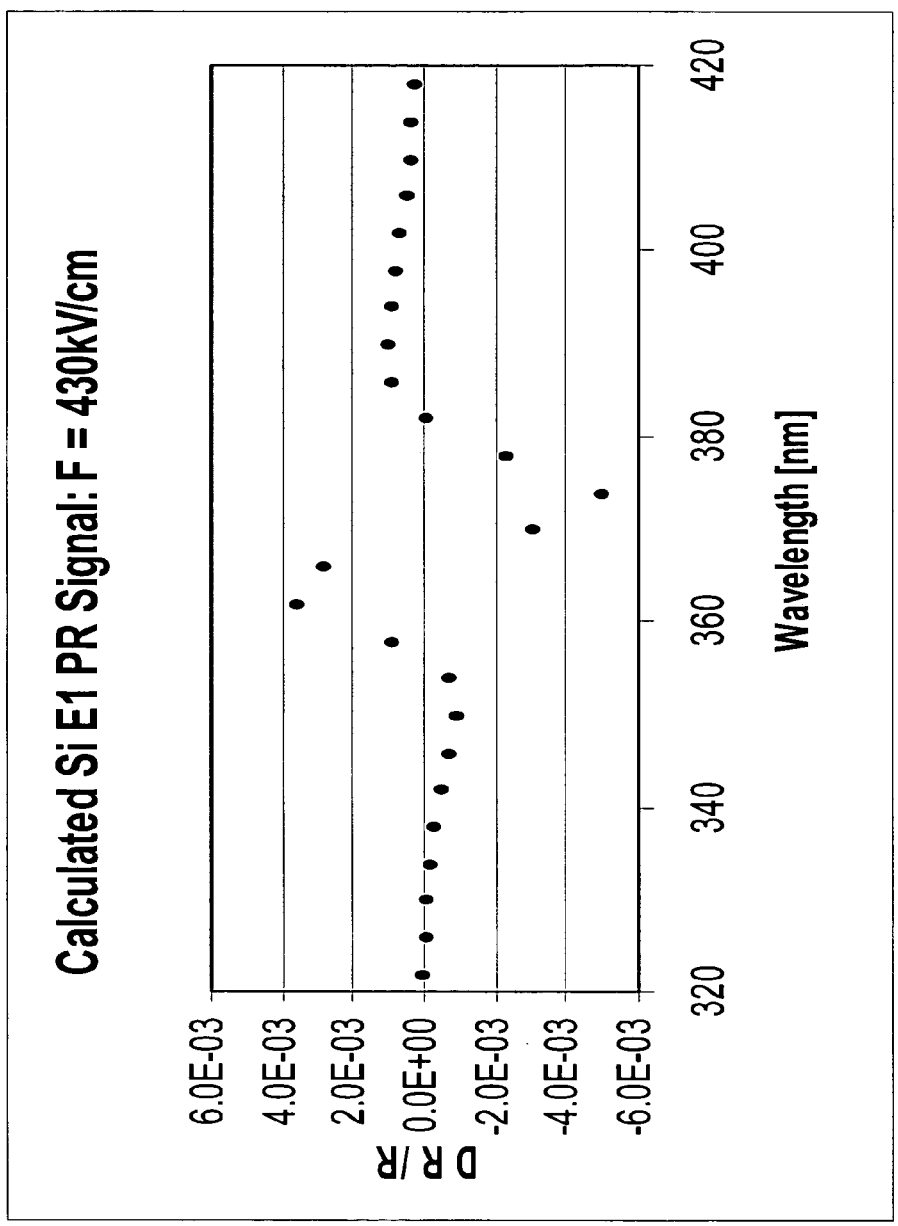
FIG. 11 is the calculated PR signal near the Si $E_1$ interband transition energy, for a pump induced space charge field of F=430 kV/cm.

As mentioned, the underlying principle of the active dopant characterization technique is to measure photo-reflectance signals occurring near strong interband transitions in the semiconductor bandstructure. FIG. 11 shows the calculated PR signal in the vicinity of the Si $E_1$ optical absorption, for an induced space charge field of F=430 kV/cm, which roughly corresponds to a pump induced carrier density of $10^{18}$/cc. This carrier density is routinely induced in commercial implant monitoring applications (Opsal, 1985). As shown in FIG. 11, over the wavelength range of approximately 360-380 nm, the amplitude of this signal is quite large. In fact, it is at least two orders of magnitude larger that the PR signals achieved in existing implant monitoring systems (Opsal, 1985). Moreover, as demonstrated below, the active dopant characterization technique may be used to differentiate and measure active dopant in Si transistor channels, while the existing systems have proven unable to implement this application.

Figure 12:
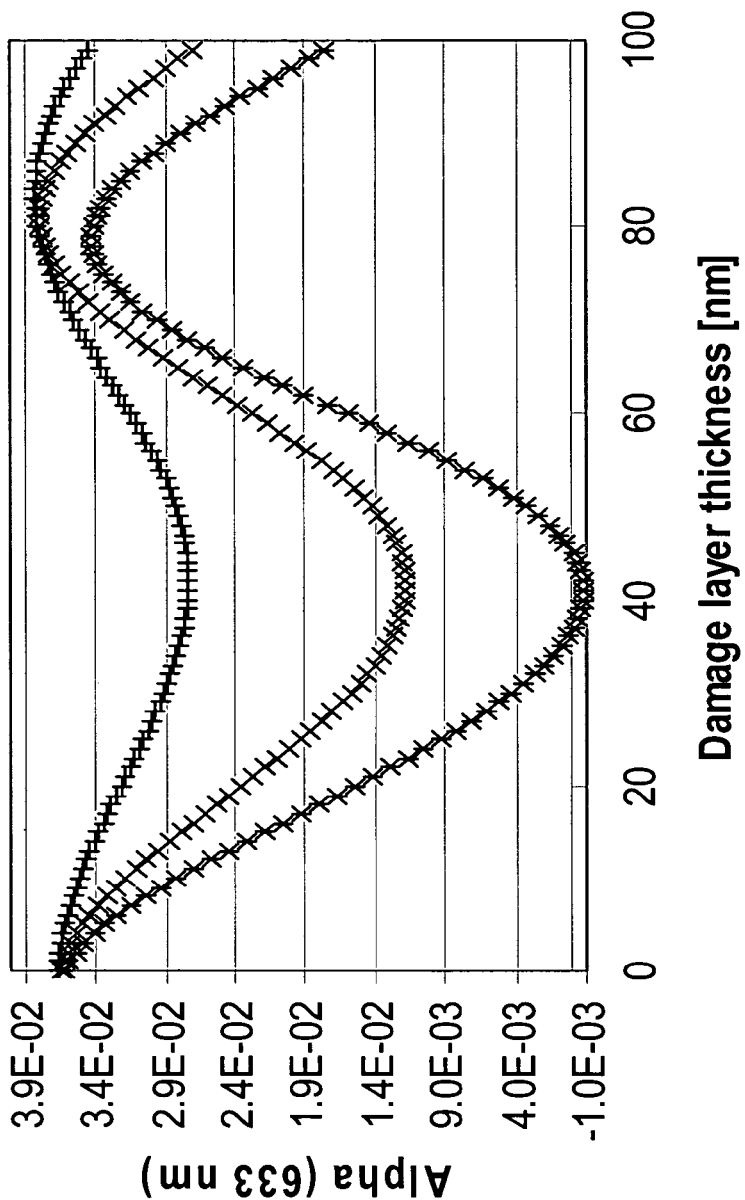
FIG. 12 is the calculated Seraphin coefficient $\alpha=\partial(\ln R)/\partial\in_1$, at $\lambda=633$ nm, of a thin implant damage layer on an optically thick silicon substrate, as a function of implant dose and depth.

In order to understand the effect of implant damage on the PR signal, it is again necessary to evaluate the Seraphin coefficients. The damage profile is responsible for the linear optical response of the material and historically has been used as a measure of the implant itself. To illustrate, consider the Seraphin coefficients for implant damaged Si, at a wavelength of 633 nm. This is the wavelength of common commercial implant monitoring PR systems (Opsal, 1985). Due to probe wavelength being located far away from any significant optical features in silicon, the photo-reflectance signal arises directly from modulation of the (Drude) carrier density. For 633 nm wavelength, only changes in the real part of the dielectric function are significant. Thus, we have $\Delta R/R \cong \alpha \Delta \in_1$, with all filmstack information contained in $\alpha$. To compute $\alpha = \partial(\ln R)/\partial \in_1$, we may first derive an analytical expression for R in terms of the indices of refraction of the damage layer, substrate, and the thickness of the damage layer. This may also be done numerically, and for any angle of incidence or polarization condition. Then R may be numerically differentiated with respect to the real part of the dielectric function, and $\alpha$ constructed. Generally, the Seraphin coefficients will oscillate with a period of $4\pi nd/\lambda$, where n is the index of refraction on the damage layer, d is the thickness of the damage layer, and $\lambda$ is the probe beam wavelength. The period depends on the path length of light in the material, and so depends also on the angle of incidence. In addition, the oscillations are damped by the absorption depth of the light. However, for normal incidence and at wavelength where Si is largely transparent, these considerations are not important. FIG. 12 shows the dependence of the Seraphin coefficient $\alpha$ on the damage layer depth and damage fraction, for a 633 nm probe beam. The top, middle, and bottom curves correspond to 10%, 30%, and 50% amorphization of the implanted layer, respectively. The periods of these cosine-like curves have been previously fit in attempts to extract junction depth sensitivity. However, in practice, the 633 nm probe loses sensitivity to implant depths of approximately 15 nm or less, as the junction depth dependence of $\Delta R/R$ contained in alpha cannot be decoupled from the dose dependence contained in $\Delta \in_1$. In particular, a simultaneous increase in both implant depth and dose can result in no change in the 633 nm probe signal. This is one reason existing tools are not effective for junction depth process control. Moreover, existing tools are severely challenged by the requirements of low dose measurements because they rely on sensitivity to intrinsically small changes in the Drude carrier dispersion.

Figure 13:
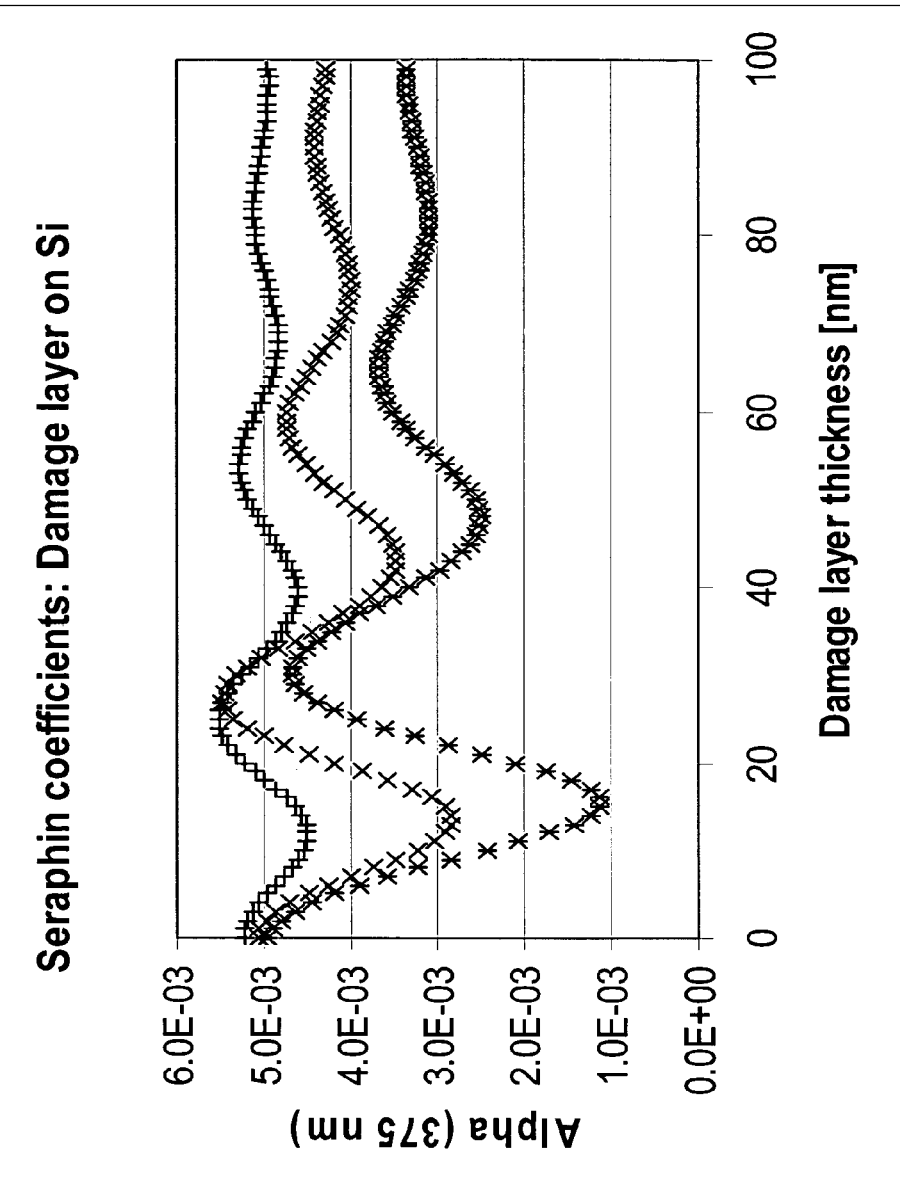
FIG. 13 is the calculated Seraphin coefficient $\alpha=\partial(\ln R)/\partial\in_1$, at $\lambda=375$ nm, of a thin implant damage layer on an optically thick silicon substrate, as a function of implant dose and depth.
Figure 14:
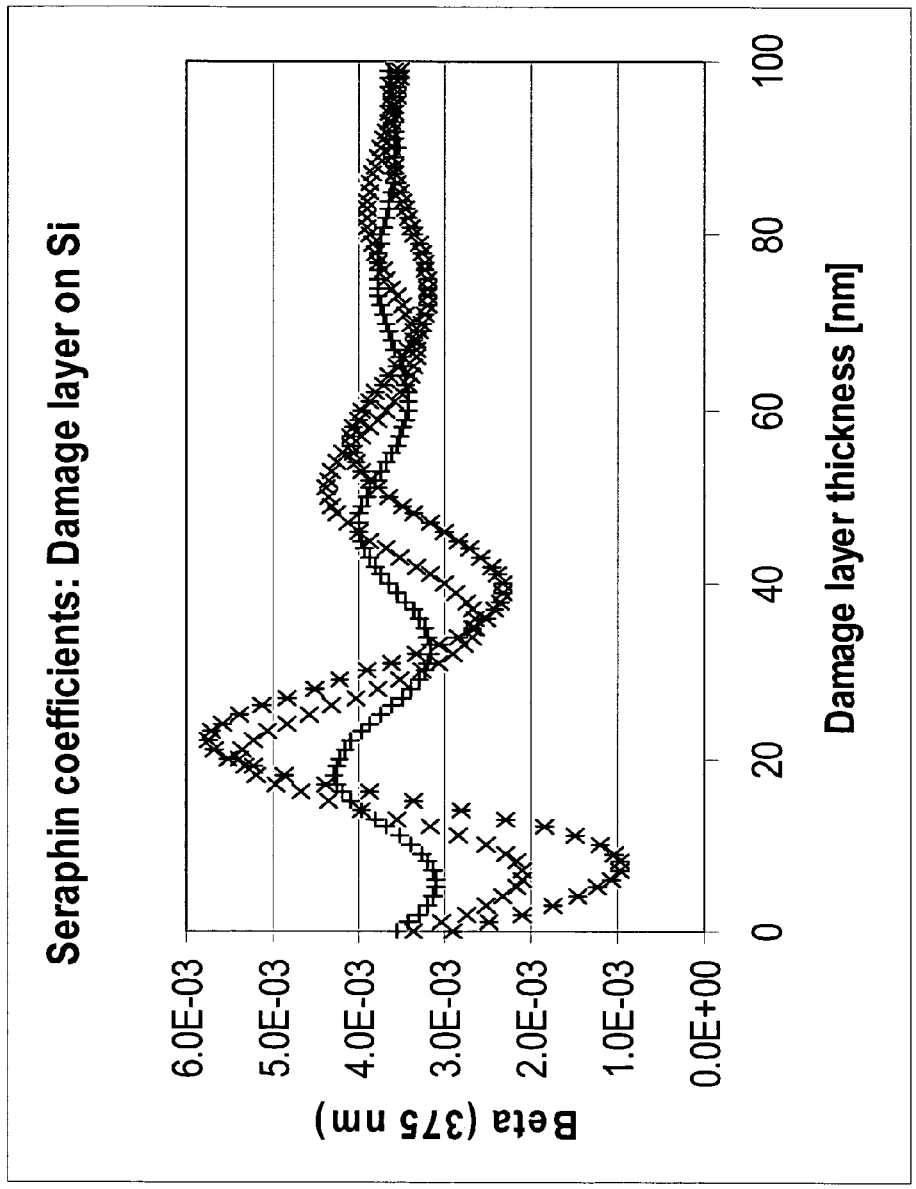
FIG. 14 is the calculated Seraphin coefficient $\beta=\partial(\ln R)/\partial\in_2$, at $\lambda=375$ nm, of a thin implant damage layer on an optically thick silicon substrate, as a function of implant dose and depth.

It is further illustrative to consider the Seraphin coefficients for implant damaged Si at wavelength 375 nm. For this wavelength, changes in both the real and imaginary part of the dielectric function are significant. Thus, we must consider both $\alpha$ and $\beta$ when determining the filmstack information contained in $\Delta R/R$. At 375 nm wavelength, the absorption depth in silicon is $\delta \cong 22.6$ nm. The absorption depth sets the depth of the PR response and hence the range over which it is important to know the effect of the filmstack on PR signal. This means that for surface film thicknesses greater than 22.6 nm, a 375 nm probe beam rapidly becomes insensitive to underlying film structure. FIG. 13 shows the dependence of the Seraphin coefficient $\alpha$ on the damage layer depth and damage fraction, for the 375 nm beam. The top, middle, and bottom curves correspond to 10%, 30%, and 50% amorphization damage, respectively. The dampening of the cosine-like curves due to absorption at this wavelength is apparent. The shorter period of oscillation of the Seraphin coefficients at 375 nm probe demonstrates this wavelength will exhibit sensitivity to junction depths down to approximately 10 nm and below (superior to the 633 nm wavelength probe). FIG. 14 shows the dependence of the Seraphin coefficient $\beta$ on the damage layer depth and damage fraction, for the 375 nm beam. The top, middle, and bottom curves correspond to 10%, 30%, and 50% amorphization, respectively.

Figure 15:
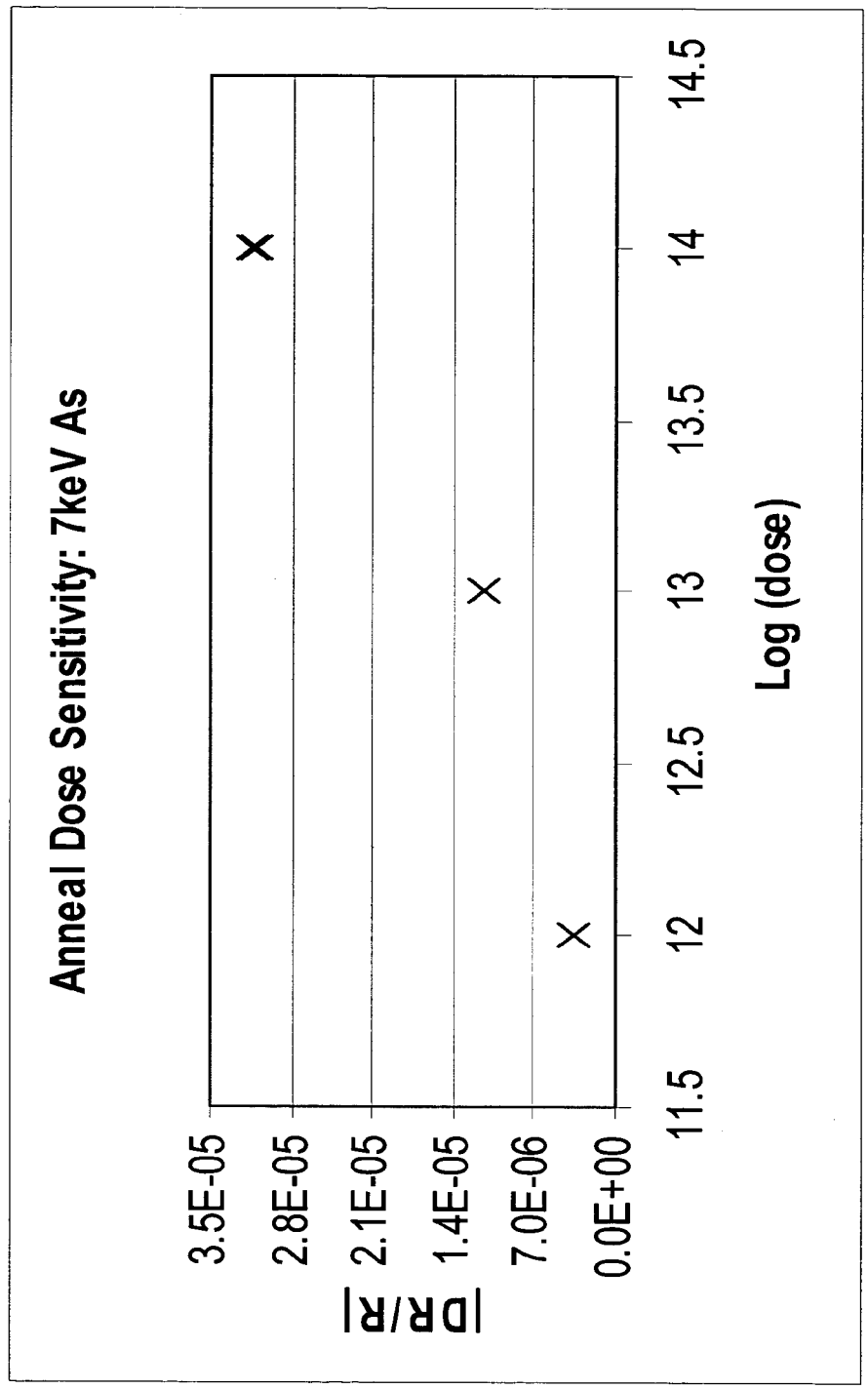
FIG. 15 is the experimental PR signal, at a modulation frequency of 2 MHz, for As implanted and annealed wafers with targeted junction depth of 10 nm.
Figure 16:
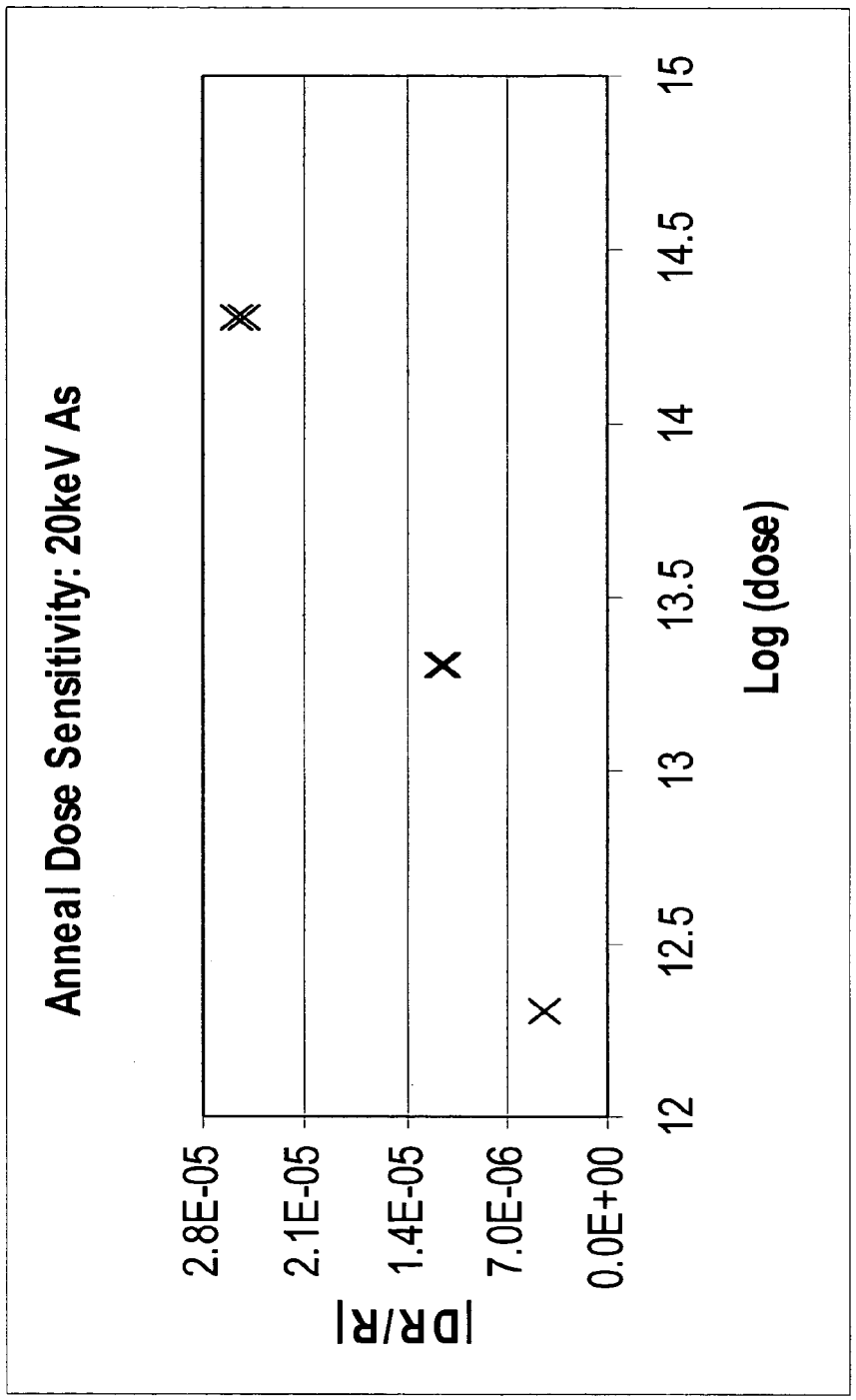
FIG. 16 is the experimental PR signal, at a modulation frequency of 2 MHz, for As implanted and annealed wafers with targeted junction depth of 20 nm.
Figure 17:
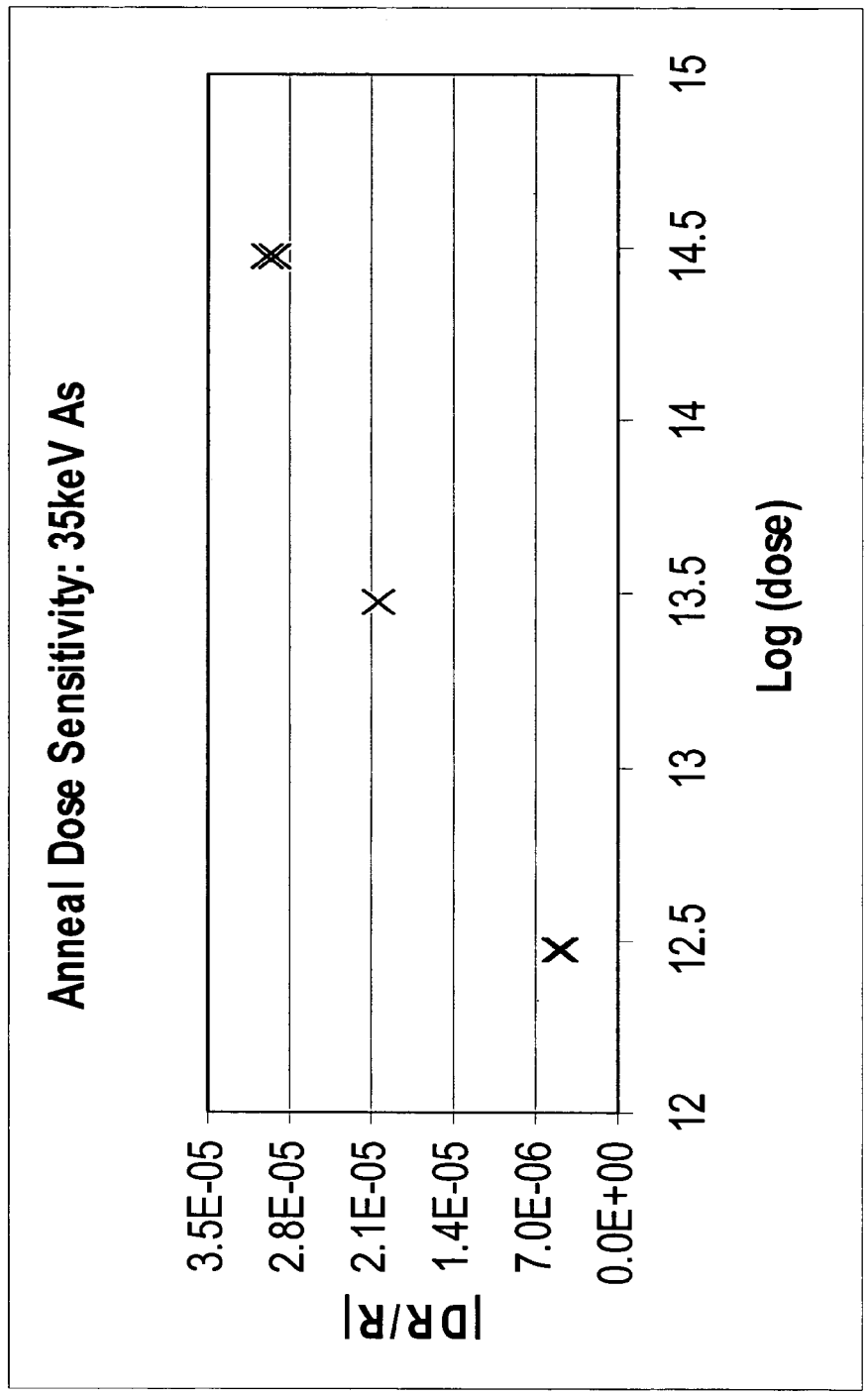
FIG. 17 is the experimental PR signal, at a modulation frequency of 2 MHz, for As implanted and annealed wafers with targeted junction depth of 30 nm.
Figure 18:
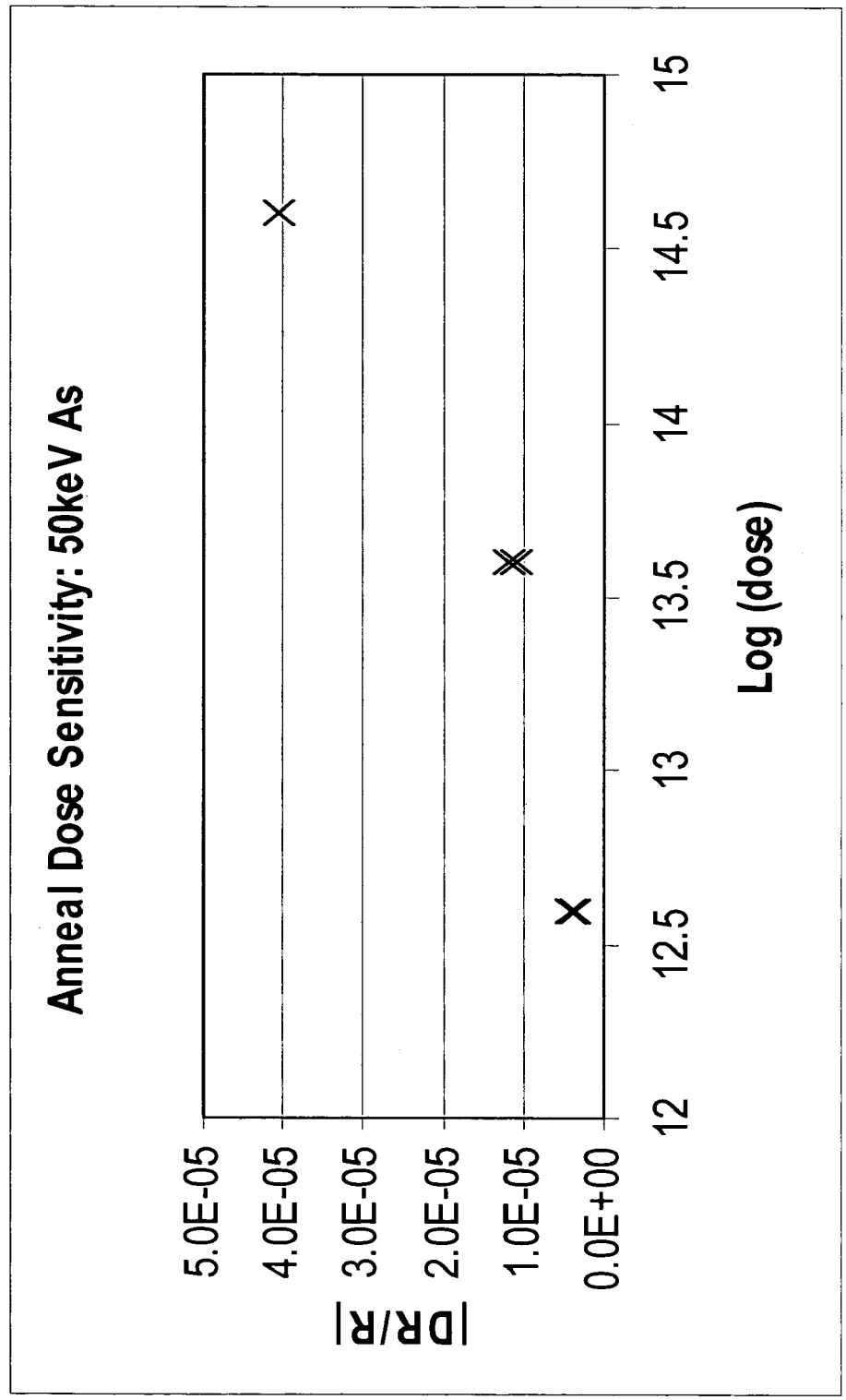
FIG. 18 is the experimental PR signal, at a modulation frequency of 2 MHz, for As implanted and annealed wafers with targeted junction depth of 40 nm.

To establish the capabilities of the active dopant characterization technique, the PR apparatus was configured with a collinear pump and probe beam with angle of incidence at 45°. The pump and probe wavelengths were 845 nm and 374 nm, respectively. The pump laser intensity was directly modulated with a 2 MHz square wave generated by the lock-in amplifier. The pump laser intensity was approximately 15 mW. The collinear pump and probe were focused using an achromatic microscope objective lens to a spot diameter of approximately 6.5 micrometers. For these conditions the carrier density generated by the pump is at least two orders of magnitude smaller than used in conventional commercial systems, or $\leq 1 \times 10^{16}$/cc. However, the greatly enhanced sensitivity of the 374 nm probe easily compensates for this reduced pump intensity, resulting in signal levels commensurate with commercial system levels. FIG. 15 shows the PR signal for wafers #2, #4, and #6. These wafers have identical 7 keV energy As implants, targeted to form a junction at 10 nm depth. Wafer #2 received a dose of $1\times10^{12}/cm^2$, wafer #4 received a dose of $1\times10^{13}/cm^2$, and wafer #6 received a dose of $1\times10^{14}/cm^2$. Each wafer received an identical anneal and is expected to be fully activated. The modulus of the PR signal |ΔR/R| rises from $\approx 3\times10^{-6}$ to $\approx 3\times10^{-5}$, or about one order of magnitude, from wafer #2 to #6. This demonstrates approximately one decade in signal change for a two decade change in dose, for a 10 nm junction depth. Thus, the PR technique demonstrates excellent sensitivity to dose in annealed wafers for the ultra-shallow junction depths required in future manufacturing processes. It may also be seen that the data is highly reproducible: the data points after load/unload almost exactly reproduce each other. Absolute measurement precision for the PR signal is $\approx 5\times10^{-7}$. FIGS. 16, 17, and 18 show similar increasing signal with dose for greater implant energies. FIG. 16 shows the PR signal for wafers #8, #10, and #12. These wafers have identical 20 keV energy As implants, targeted to form a junction at 20 nm depth. Wafer #8 received a dose of $2\times10^{12}/cm^2$, wafer #10 received a dose of $2\times10^{13}/cm^2$, and wafer #12 received a dose of $2\times10^{14}/cm^2$. Each wafer received an identical anneal and is expected to be fully activated. The modulus of the PR signal rises from $\approx 4\times10^{-6}$ to $\approx 2.6\times10^{-5}$, or about one order of magnitude, from wafer #8 to #12. This again demonstrates excellent PR sensitivity to dose, and excellent signal reproducibility, in annealed wafers for ultra-shallow junction depths of 20 nm. FIG. 17 shows the PR signal for wafers #14, #16, and #18. These wafers have identical 35 keV energy implants, targeted to form a junction at 30 nm depth. Wafer #14 received a dose of $3\times10^{12}/cm^2$, wafer #16 received a dose of $3\times10^{13}/cm^2$, and wafer #18 received a dose of $3\times10^{14}/cm^2$. Each wafer received an identical anneal and is expected to be fully activated. The modulus of the PR signal |ΔR/R| rises from $\approx 5\times10^{-6}$ to $\approx 3\times10^{-5}$, or about one order of magnitude, from wafer #14 to #18. This again demonstrates excellent PR sensitivity to dose, and excellent signal reproducibility, in annealed wafers for ultra-shallow junction depths of 30 nm. FIG. 18 shows the PR signal for wafers #20, #22, and #24. These wafers have identical 50 keV energy implants, targeted to form a junction at 40 nm depth. Wafer #20 received a dose of $4\times10^{12}/cm^2$, wafer #22 received a dose of $4\times10^{13}/cm^2$, and wafer #24 received a dose of $4\times10^{14}/cm^2$. Each wafer received an identical anneal and is expected to be fully activated. The modulus of the PR signal rises from $\approx 4\times10^{-6}$ to $\approx 4\times10^{-5}$, or about one order of magnitude, from wafer #20 to #24. This again demonstrates the excellent PR sensitivity to dose, and excellent signal reproducibility, in annealed wafers for ultra-shallow junction depths of 40 nm.

Figure 19:
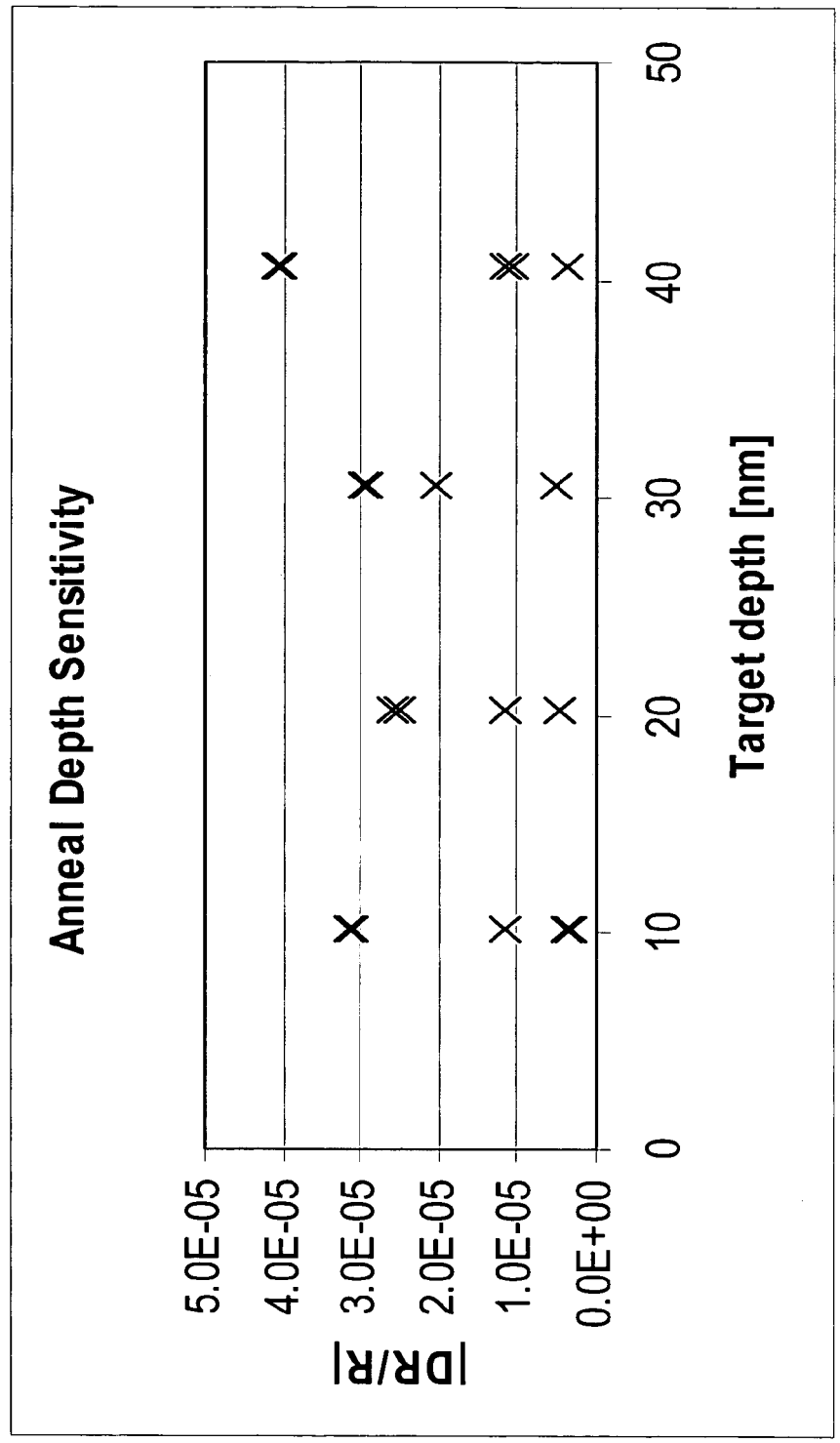
FIG. 19 is the experimental PR signal for As implanted and annealed wafers, as shown in FIGS. 15-18, plotted as a function of junction depth.
Figure 20:
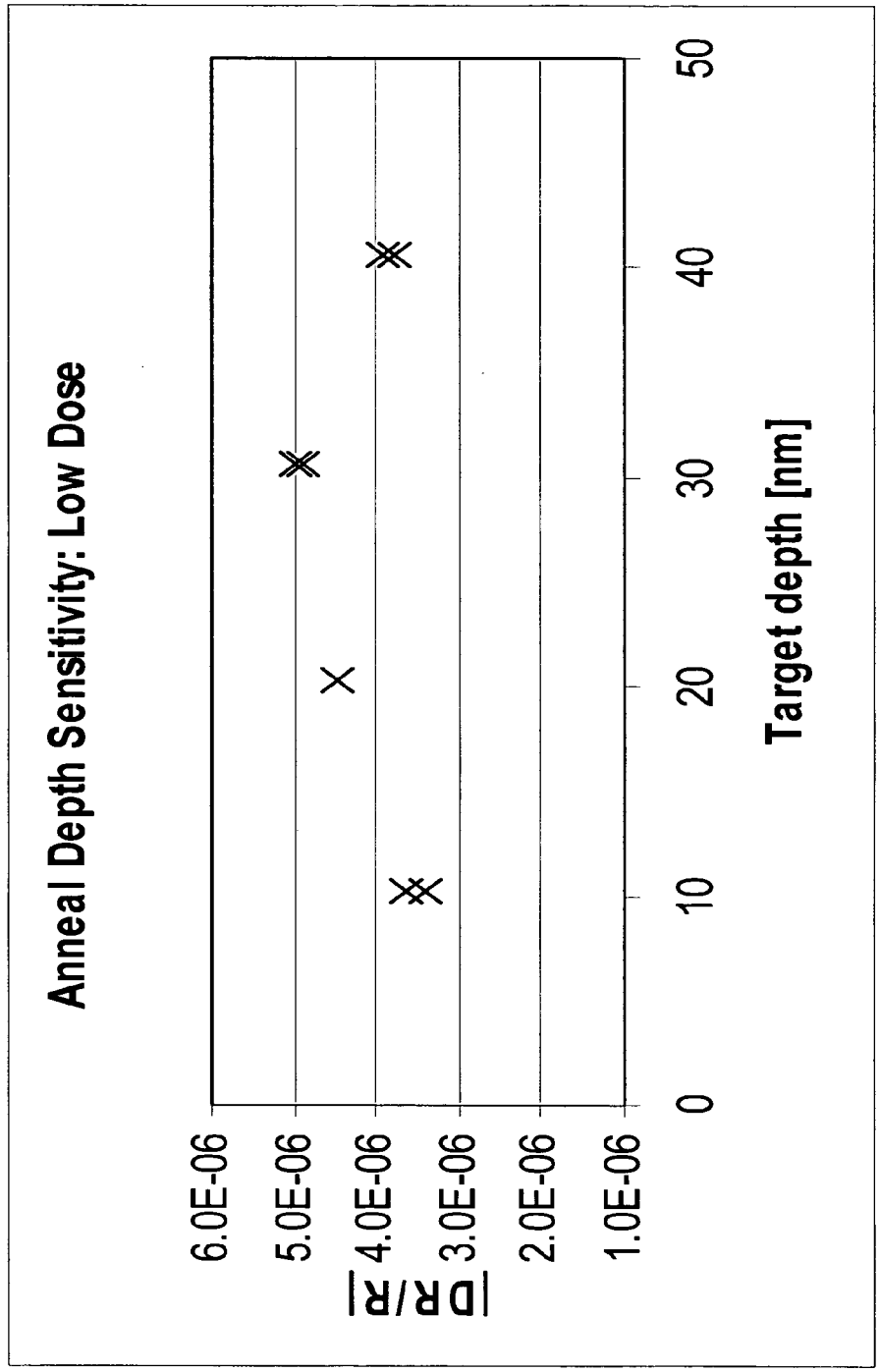
FIG. 20 is the experimental PR signal for "low dose" As implanted and annealed wafers, as shown in FIGS. 15-18, plotted as a function of junction depth.

As discussed earlier, a sinusoidal variation of PR signal is expected with junction depth. FIG. 19 shows the modulus of the PR signal for the each of the annealed wafers as a function of junction depth. Each of the three "rows" in FIG. 19, which correspond to approximately constant doping densities of $1\times10^{18}/cc$, $1\times10^{19}/cc$, and $1\times10^{20}/cc$, exhibit such a sinusoidal variation. FIG. 20 further demonstrates this characteristic of the PR data for the lowest dose, by scaling the lowest density row of FIG. 19.

Figure 21:
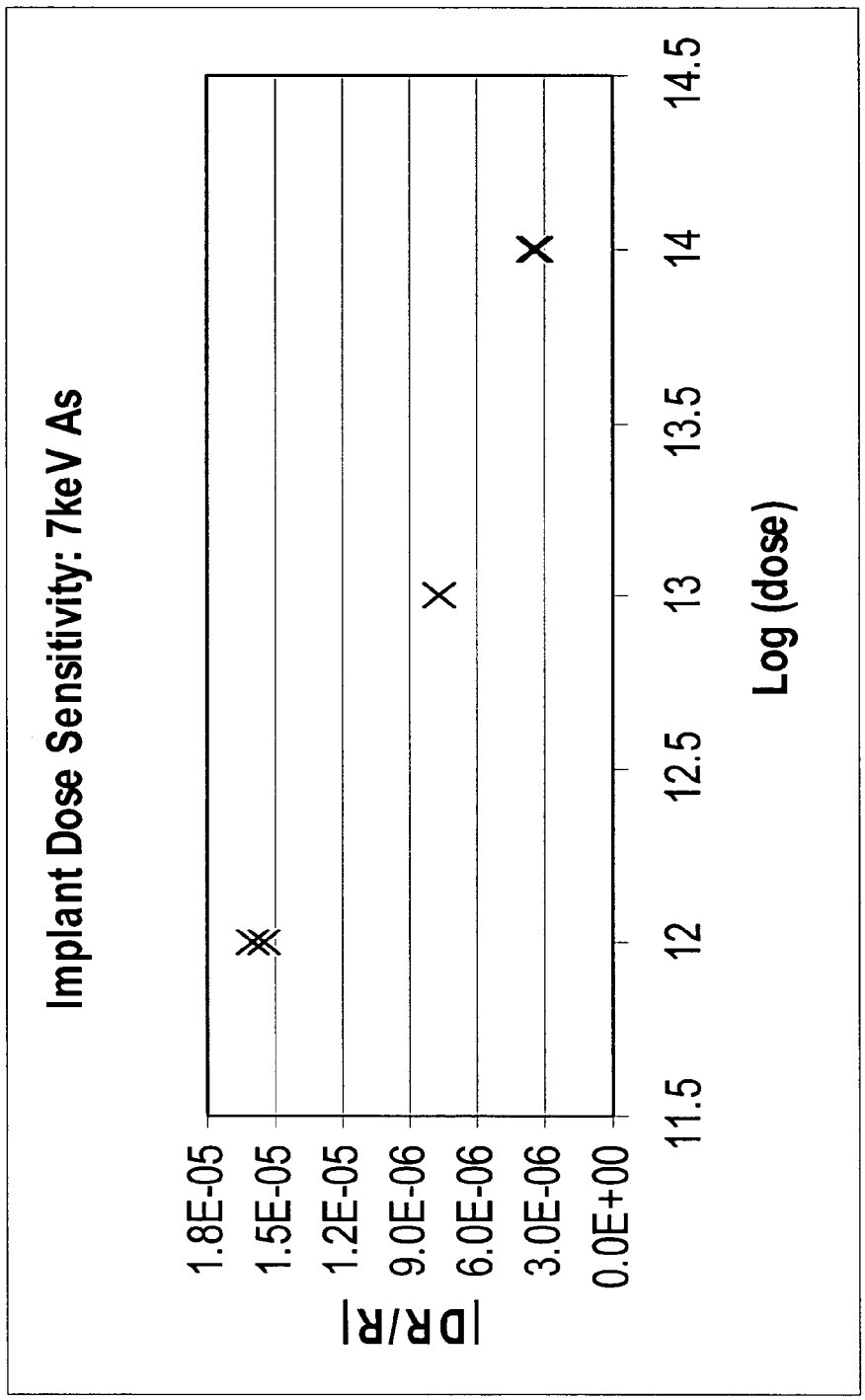
FIG. 21 is the experimental PR signal, at a modulation frequency of 2 MHz, for As "implant only" (no anneal) wafers with targeted junction depth of 10 nm.
Figure 22:
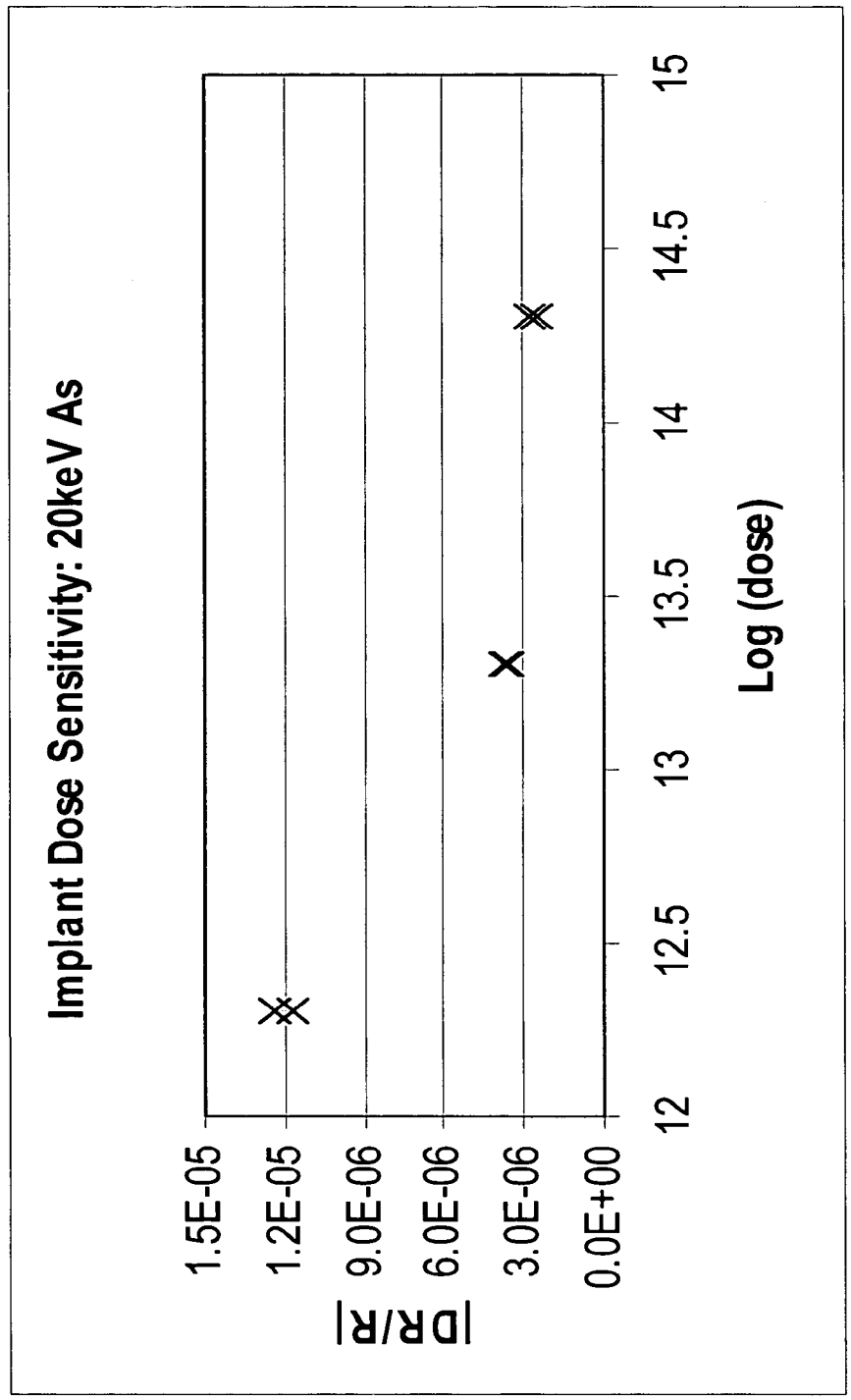
FIG. 22 is the experimental PR signal, at a modulation frequency of 2 MHz, for As "implant only" wafers with targeted junction depth of 20 nm.
Figure 23:
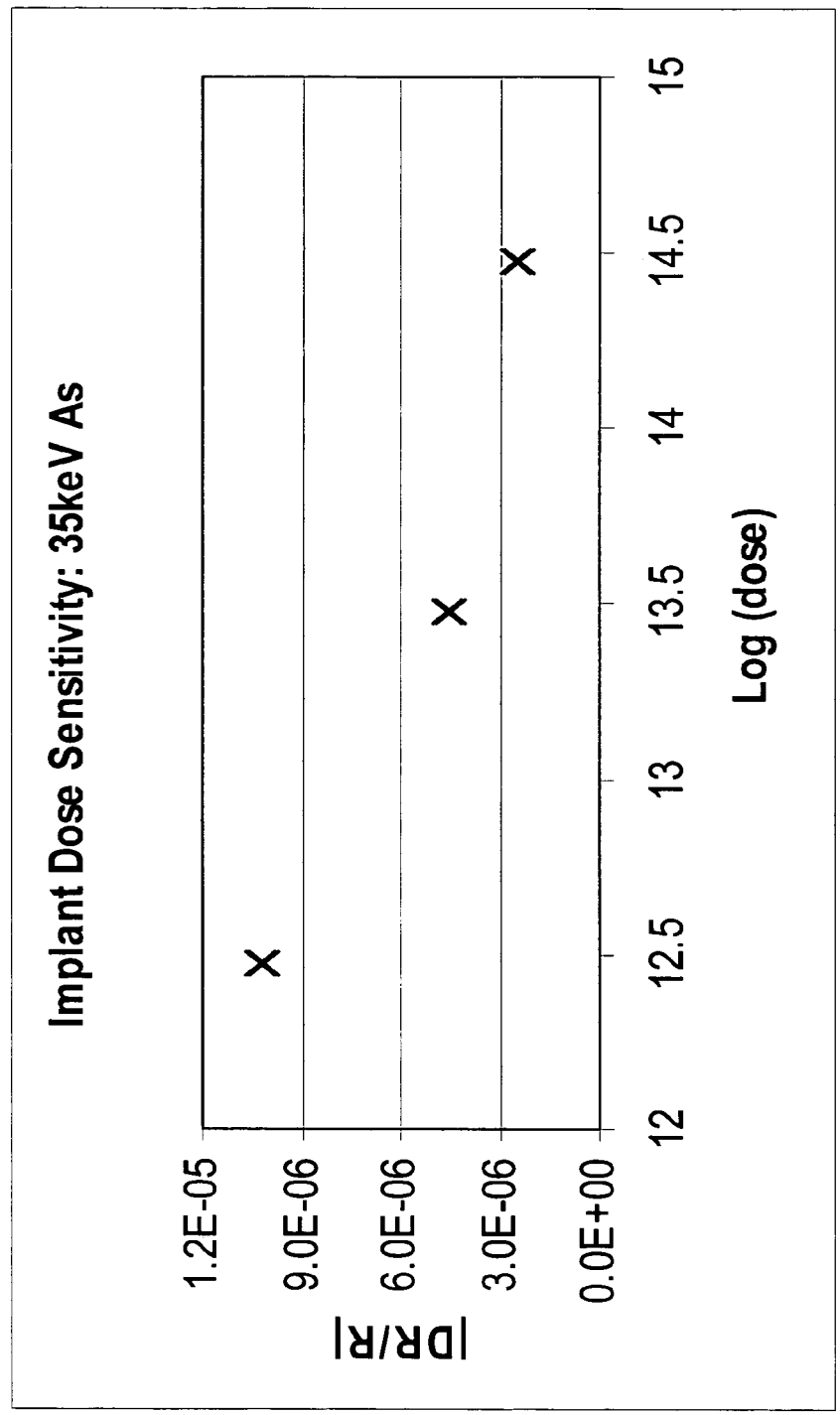
FIG. 23 is the experimental PR signal, at a modulation frequency of 2 MHz, for As "implant only" wafers with targeted junction depth of 30 nm.
Figure 24:
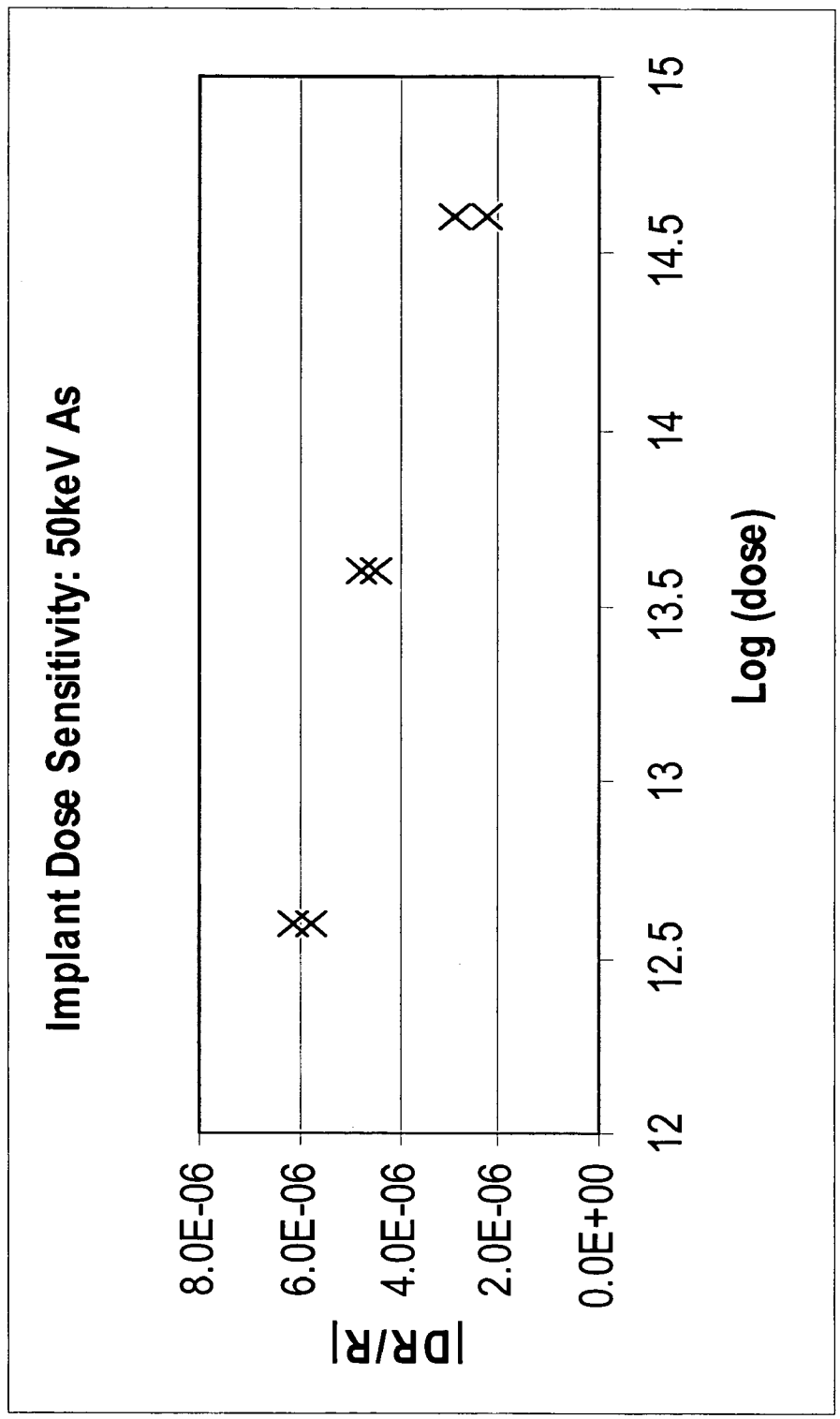
FIG. 24 is the experimental PR signal, at a modulation frequency of 2 MHz, for As "implant only" wafers with targeted junction depth of 40 nm.

FIG. 21 shows the PR signal for wafers #1, #3, and #5. These are the "implant only" wafers with no anneal. They have identical 7 keV energy As implants, targeted to form a junction at 10 nm depth. Wafer #1 received a dose of $1\times10^{12}/cm^2$, wafer #3 received a dose of $1\times10^{13}/cm^2$, and wafer #5 received a dose of $1\times10^{14}/cm^2$. The modulus of the PR signal |ΔR/R| decreases from $\approx 1.6\times10^{-5}$ to $\approx 3\times10^{-6}$, about an order of magnitude, from wafer #1 to #5. This decrease in the signal with increasing dose, which is opposite the behavior observed for the annealed wafers, is due to the damage from the implant reducing the sharpness of the crystalline Si $E_1$ interband transition energy. This demonstrates excellent PR sensitivity to dose in "implant only" wafers for ultra-shallow junction depths of 10 nm. FIGS. 22, 23, and 24 show similar decreasing signal with dose for greater implant energies. FIG. 22 shows the PR signal for wafers #7, #9, and #11. These wafers have identical 20 keV energy As implants, targeted to form a junction at 20 nm depth. Wafer #7 received a dose of $2\times10^{12}/cm^2$, wafer #9 received a dose of $2\times10^{13}/cm^2$, and wafer #11 received a dose of $2\times10^{14}/cm^2$. Each wafer is "implant only" with no anneal. The modulus of the PR signal |ΔR/R| decreases from $\approx 1.2\times10^{-5}$ to $\approx 3\times10^{-6}$, about a factor of 4, from wafer #7 to #11. This demonstrates good PR sensitivity to dose in "implant only" wafers for ultra-shallow junction depths of 20 nm. FIG. 23 shows the PR signal for wafers #13, #15, and #17. These wafers have identical 35 keV energy As implants, targeted to form a junction at 30 nm depth. Wafer #13 received a dose of $3\times10^{12}/cm^2$, wafer #15 received a dose of $3\times10^{13}/cm^2$, and wafer #17 received a dose of $3\times10^{14}/cm^2$. Each wafer is "implant only" with no anneal. The modulus of the PR signal |ΔR/R| decreases from $\approx 1\times10^{-5}$ to $\approx 2\times10^{-6}$, about a factor of 5, from wafer #13 to #17. This again demonstrates good PR sensitivity to dose in "implant only" wafers for ultra-shallow junction depths of 30 nm. FIG. 24 shows the PR signal for wafers #19, #21, and #23. These wafers have identical 50 keV energy As implants, targeted to form a junction at 40 nm depth. Wafer #19 received a dose of $4\times10^{12}/cm^2$, wafer #21 received a dose of $4\times10^{13}/cm^2$, and wafer #23 received a dose of $4\times10^{14}/cm^2$. Each wafer is "implant only" with no anneal. The modulus of the PR signal |ΔR/R| decreases from $\approx 6\times10^{-6}$ to $\approx 2\times10^{-6}$, about a factor of 3, from wafer #19 to #23. This demonstrates reasonable PR sensitivity to dose in "implant only" wafers for ultra-shallow junction depths of 40 nm.

Figure 25:
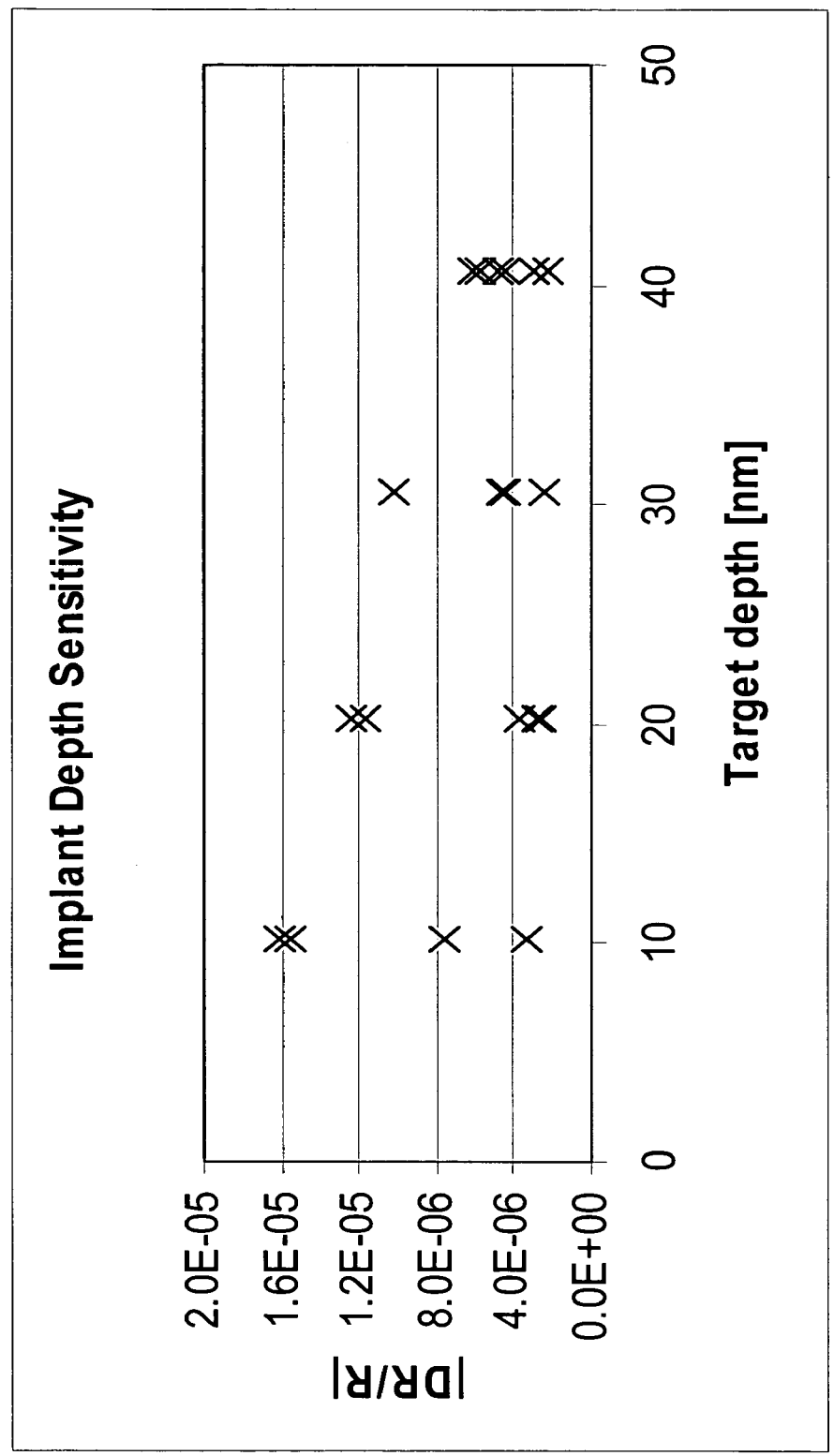
FIG. 25 is the experimental PR signal for is the experimental PR signal for As "implant only" wafers, as shown in FIGS. 21-24, plotted as a function of junction depth.

FIG. 25 shows the modulus of the PR signal for the each of the as implanted wafers as a function of junction depth. By following each "row" in FIG. 25, it is seen that each set of targeted doping densities ($1\times10^{18}/cc$, $1\times10^{19}/cc$, and $1\times10^{20}/cc$) follows a damped sinusoidal variation. The observed decreasing sensitivity to dose with implant depth is due to a combination of decreasing crystallinity and greater total absorption within the damage layer.

Therefore, as disclosed herein, the method of photo-reflectance characterization of strain and active dopant in semiconductor structures provides a new and precise capability to differentiate and measure strain and active dopant in semiconductor nanostructures, and in so doing, substantially departs from the conventional concepts and designs of the prior art.

As to a further discussion of the manner of usage and operation of the present disclosure, the same should be apparent from the above description. Accordingly, no further discussion relating to the manner of usage and operation will be provided.

With respect to the above description then, it is to be realized that the optimum dimensional relationships for the parts of the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accord-

REFERENCES

U.S. Patent Documents:

| | | | |
|---|---|---|---|
| 6,963,402 | November 2005 | Chism | 356/367 |
| 6,195,166 | February 2001 | Gray | 356/477 |
| 4,931,132 | June 1990 | Aspnes | 156/601 |

Other Publications:

"Dynamics of the plasma and thermal waves in surface-modified semiconductors (invited)," Alex Salnick and Jon Opsal, Rev. Sci. Inst. 74, 545 (2003).

"Nondestructive profile measurements of annealed shallow implants," P. Borden, et al., J. Vac. Sci. Technol. B 18, 602 (2000).

"Dielectric response of strained and relaxed $Si_{1-x-y}Ge_xC_y$ alloys grown by molecular beam epitaxy on Si(001)," R. Lange et al., J. Appl. Phys. 80, 4578 (1996).

"Optical functions of ion-implanted, laser-annealed heavily doped silicon," G. E. Jellison et al., Phys. Rev. B 52, 14 607 (1995).

"Modulation Spectroscopy of Semiconductors and Semiconductor Microstructures," F. H. Pollack, in *Handbook on Semiconductors*, Vol. 2, edited by M. Balkanski, pp. 527-635 (North-Holland, Amsterdam, 1994).

"Photo-reflectance characterization of GaAs as a function of temperature, carrier concentration, and near-surface electric field," A. Badakhshan et al., J. Vac. Sci. Technol. B 11, 169 (1993).

"Photo-reflectance study of photovoltage effects in GaAs diode structures," V. M. Airaksinen and H. K. Lipsanen, Appl. Phys. Lett. 60, 2110 (1992).

"Photo-reflectance studies of silicon films on sapphire," A. Giordana and R. Glosser, J. Appl. Phys. 69, 3303 (1991).

"Correlation between the photo-reflectance response at $E_1$ and carrier concentration in n- and p-GaAs," A. Badakhshan, R. Glosser, and S. Lambert, J. Appl. Phys. 69, 2525 (1991).

"Dynamics of photo-reflectance from undoped GaAs," H. Shen et al., Appl. Phys. Lett. 59, 321 (1991).

"Photo-reflectance study of surface Fermi level in GaAs and GaAlAs," H. Shen et al., Appl. Phys. Lett. 57, 2118 (1990).

"Generalized Franz-Keldysh theory of electromodulation," H. Shen and F. H. Pollak, Phys. Rev. B 42, 7097 (1990).

"Photo-reflectance study of Fermi level changes in photo-washed GaAs," H. Shen, F. H. Pollak, and J. M. Woodall, J. Vac. Sci. Technol. B 8, 413 (1990).

"Electric field distributions in a molecular-beam epitaxy $Ga_{0.83}Al_{0.17}As$/GaAs/GaAs structure using photo-reflectance," H. Shen, F. H. Pollak, J. M. Woodall, and R. N. Sacks, J. Vac. Sci. Technol. B 7, 804 (1989).

"Thermal and plasma wave depth profiling in silicon," Jon Opsal and Allan Rosencwaig, Appl. Phys. Lett. 47, 498 (1985).

"Photo-reflectance characterization of interband transitions in GaAs/AlGaAs multiple quantum wells and modulation-doped heterojunctions," O. J. Glembocki et al., Appl. Phys. Lett. 46, 970 (1985).

"Modulation Spectroscopy," D. Aspnes, in *Handbook on Semiconductors*, Vol. 2, edited by M. Balkanski, pp. 109 (North-Holland, Amsterdam, 1980).

"Photo-reflectance Line Shape at the Fundamental Edge in Ultrapure GaAs," J. L. Shay, Phys. Rev. B 2, 803 (1970).

"Reflectance Modulation by the Surface Field in GaAs," R. E. Nahory and J. L. Shay, Phys. Rev. Lett. 21, 1569 (1968).

"Band-Structure Analysis from Electro-Reflectance Studies," B. O. Seraphin and N. Bottka, Phys. Rev. 145, 628 (1966).

"Optical Field Effect in Silicon," B. O. Seraphin, Phys. Rev. 140, A 1716 (1965).

"Optical-Field Effect on Thresholds, Saddle-Point Edges, and Saddle-Point Excitons," J. C. Philips and B. O. Seraphin, Phys. Rev. Lett. 15, 107 (1965).

"Field Effect of the Reflectance in Silicon," B. O. Seraphin and N. Bottka, Phys. Rev. Lett. 15, 104 (1965).

The invention claimed is:

1. A method of determining physical properties of a semiconductor structure, the method comprising the steps of:
   a) illuminating an area of a surface of the semiconductor structure using an amplitude modulated pump laser beam, the pump beam containing at least one wavelength with energy greater than the smallest interband transition energy of a semiconductor material within the semiconductor structure, thereby inducing time periodic changes in the electronic charge density within the semiconductor structure such that the electric field within the semiconductor structure obtains a time periodic modulation, and wherein semiconductor material within the semiconductor structure is subject to a time periodic modulation of interband transition energies;
   b) illuminating a portion of said area of step a) with a separate probe laser beam, the probe beam containing at least one wavelength nearby an interband transition energy of a semiconductor material within the semiconductor structure, and suitable for recording the induced changes in semiconductor material optical response which occur nearby to interband transition energies;
   c) recording the reflected alternating current probe light from the illumination of the semiconductor structure, wherein the alternating current probe light contains the induced changes in the semiconductor material optical response, known as the photo-reflectance signal; and
   d) using the information collected in steps a), b), and c) to determine physical properties of the semiconductor structure.

2. The method as defined in claim 1, wherein the physical strain is monitored according to an empirically determined calibration curve relating the sign and amplitude of the normalized photo-reflectance signal to the physical strain.

3. The method as defined in claim 1, wherein the physical strain is monitored according to the relation $\Delta R/R = m\chi + b$, where $\Delta R/R$ is the normalized photo-reflectance signal, $\chi$ is the physical strain, m is an empirically determined linear correlation coefficient, and b is an empirically determined offset.

4. The method as defined in claim 1, wherein the electronic charge density is monitored according to an empirically determined calibration curve relating the normalized photo-reflectance signal to the electronic charge density.

5. The method as defined in claim 1, wherein the electronic charge density is monitored according to the relation $\Delta R/R = mN_e + b$, where $\Delta R/R$ is the normalized photo-reflectance signal, $N_e$ is the charge density, m is an empirically determined linear correlation coefficient, and b is an empirically determined offset.

6. The method as defined in claim 1, wherein the electric field is monitored according to the relation $\Delta R/R = mF^2 + b$, where $\Delta R/R$ is the normalized photo-reflectance signal, F is the electric field, m is an empirically determined linear correlation coefficient, and b is an empirically determined offset.

7. The method as defined in claim 1, wherein the electronic charge depth profile is monitored according to an empirically determined calibration curve relating the normalized photo-reflectance signal to the electronic charge depth profile.

8. The method as defined in claim 1, wherein the probe laser is a tunable wavelength laser providing a multiplicity of wavelengths nearby to at least one interband transition energy in the optical response of the semiconductor material, and wherein alternating current probe light wavelength information is used to determine position, amplitude, spectral width, and/or spectral shape of the interband transition energy.

9. The method as defined in claim 1, wherein the semiconductor structure comprises a semiconductor-on-insulator filmstructure and wherein the wavelength of the pump beam is selected to provide an absorption depth less than or commensurate with the thickness of the electrically insulated semiconductor layer, and therefore suitable for inducing time periodic changes in the electronic charge density within the insulated semiconductor layer.

10. The method as defined in claim 1, wherein the semiconductor structure comprises an electrically insulated semiconductor material and wherein the wavelength of the pump beam is selected to provide an absorption depth less than or commensurate with the physical dimensions of the semiconductor material, and therefore suitable for inducing time periodic changes in the electronic charge density within the insulated semiconductor material.

11. The method as defined in claim 1, wherein changes in the in photo-reflectance signal as a function of pump beam intensity are determined.

12. Apparatus for detecting physical properties of a semiconductor structure, comprising:
 a semiconductor structure with a reflecting surface;
 a pump laser system, providing an amplitude modulated laser beam with a modulation frequency in the range of 100 kHz to 50 MHz, operating at optical powers of approximately 5 mW or greater, and containing at least one wavelength with energy greater than the smallest interband transition energy of a semiconductor material within the semiconductor structure;
 a probe laser system, providing a continuous wave laser beam, operating at optical powers of approximately 10 mW or less, and containing at least one wavelength nearby an interband transition energy of a semiconductor material within the semiconductor structure;
 an optical system effective to focus either laser beam onto a common focal spot on a surface of the semiconductor structure of diameter 50 microns or less, and to separate and direct probe light reflected from the sample into a photoreceiver;
 a photoreceiver configured to generate an electrical current proportional to the input intensity;
 a phase locked signal detection system connected to record the photoreceiver output; and
 a computer with measurement and system control software.

13. The apparatus of claim 12, wherein the semiconductor structure comprises a silicon-on-insulator substrate and the pump laser wavelength is approximately 500 nm, or less.

14. The apparatus of claim 12, wherein the probe laser wavelength is approximately 375 nm.

15. The apparatus of claim 12, wherein the probe laser is an external cavity tunable wavelength laser providing a multiplicity of wavelengths nearby to an interband transition energy of a semiconductor material within the semiconductor structure.

16. The apparatus of claim 12, wherein the pump and probe laser beams are made collinear through the use of a dichroic beamsplitter.

17. The apparatus of claim 16, wherein the collinear pump and probe laser beams are co-focused onto an area of a surface of the semiconductor structure using an achromatic objective lens.

18. The apparatus of claim 12, wherein the pump light is separated from the reflected alternating current probe light by the use of a color filter.

19. The apparatus of claim 12, wherein the pump laser intensity is directly modulated with a reference signal generated internal to the phase locked detection system.

* * * * *